(12) United States Patent
Park et al.

(10) Patent No.: US 9,221,820 B2
(45) Date of Patent: Dec. 29, 2015

(54) HETEROCYCLIC COMPOUND AND ORGANIC LIGHT EMITTING DEVICE USING THE SAME

(71) Applicant: LG Chem, Ltd., Seoul (KR)

(72) Inventors: Tae Yoon Park, Daejeon (KR); Minseung Chun, Daejeon (KR); Dongheon Kim, Daejeon (KR); Jiyeon Ahn, Daejeon (KR); Hyoung Seok Kim, Daejeon (KR)

(73) Assignee: LG CHEM, LTD., Seoul (KR)

( * ) Notice: Subject to any disclaimer, the term of this patent is extended or adjusted under 35 U.S.C. 154(b) by 0 days.

(21) Appl. No.: 14/373,541

(22) PCT Filed: Feb. 7, 2014

(86) PCT No.: PCT/KR2014/001073
§ 371 (c)(1),
(2) Date: Jul. 21, 2014

(87) PCT Pub. No.: WO2014/123391
PCT Pub. Date: Aug. 14, 2014

(65) Prior Publication Data
US 2015/0259347 A1    Sep. 17, 2015

(30) Foreign Application Priority Data
Feb. 7, 2013    (KR) .......................... 10-2013-0013868

(51) Int. Cl.
| | | |
|---|---|---|
| *H01L 51/54* | (2006.01) | |
| *C09K 11/06* | (2006.01) | |
| *C07D 471/10* | (2006.01) | |
| *C07F 9/6561* | (2006.01) | |
| *C07D 471/20* | (2006.01) | |
| *H01L 51/50* | (2006.01) | |
| *H01L 51/00* | (2006.01) | |
| *C07D 209/82* | (2006.01) | |
| *C07F 9/00* | (2006.01) | |
| *H01L 51/52* | (2006.01) | |

(52) U.S. Cl.
CPC ............ *C07D 471/20* (2013.01); *C07D 209/82* (2013.01); *C07D 471/10* (2013.01); *C07F 9/00* (2013.01); *C07F 9/6561* (2013.01); *C09K 11/06* (2013.01); *H01L 51/0072* (2013.01); *H01L 51/50* (2013.01); *C09K 2211/1007* (2013.01); *C09K 2211/1011* (2013.01); *C09K 2211/1014* (2013.01); *C09K 2211/1029* (2013.01); *C09K 2211/1044* (2013.01); *H01L 51/0085* (2013.01); *H01L 51/5012* (2013.01); *H01L 51/5016* (2013.01); *H01L 51/5056* (2013.01); *H01L 51/5072* (2013.01); *H01L 51/5088* (2013.01); *H01L 51/5092* (2013.01); *H01L 51/5206* (2013.01); *H01L 51/5221* (2013.01); *H01L 2251/301* (2013.01); *H01L 2251/308* (2013.01)

(58) Field of Classification Search
None
See application file for complete search history.

(56) References Cited

U.S. PATENT DOCUMENTS

| | | |
|---|---|---|
| 4,539,507 A | 9/1985 | VanSlyke et al. |
| 2007/0247059 A1* | 10/2007 | Cho et al. ...................... 313/499 |
| 2007/0292715 A1* | 12/2007 | Yoon et al. .................... 428/690 |
| 2009/0121625 A1 | 5/2009 | Ohrui et al. |
| 2010/0019658 A1* | 1/2010 | Lin et al. ........................ 313/504 |
| 2011/0272681 A1 | 11/2011 | Sugimoto et al. |
| 2012/0068170 A1 | 3/2012 | Pflumm et al. |
| 2012/0175561 A1 | 7/2012 | Franz et al. |
| 2012/0228552 A1 | 9/2012 | Parham et al. |
| 2012/0228554 A1 | 9/2012 | Franz et al. |
| 2012/0238105 A1 | 9/2012 | Anemian et al. |
| 2013/0082209 A1 | 4/2013 | Stoessel et al. |

FOREIGN PATENT DOCUMENTS

| | | | |
|---|---|---|---|
| KR | 10-2009-0035637 A | 4/2009 | |
| KR | 10-2010-0130197 A | 12/2010 | |
| KR | 10-2011-0117063 A | 10/2011 | |
| KR | 1020120015883 A | 2/2012 | |
| WO | 2011/076314 A1 | 6/2011 | |

* cited by examiner

*Primary Examiner* — Andrew K Bohaty
(74) *Attorney, Agent, or Firm* — Dentons US LLP

(57) ABSTRACT

The present specification provides a heterocyclic compound, and an organic light emitting device including: a first electrode, a second electrode, and organic material layers formed of one or more layers including a light emitting layer disposed between the first electrode and the second electrode, in which one or more layers of the organic material layers include the heterocyclic compound or a compound in which a heat-curable or photo-curable functional group is introduced into the heterocyclic compound.

12 Claims, 2 Drawing Sheets

HETEROCYCLIC COMPOUND AND ORGANIC LIGHT EMITTING DEVICE USING THE SAME

CROSS-REFERENCE TO RELATED APPLICATIONS

This application is a 35 U.S.C. §371 National Phase entry of International Application No. PCT/KR2014/001073, filed Feb. 7, 2014, which claims priority to and the benefit of Korean Patent Application No. 10-2013-0013868 filed in the Korean Intellectual Property Office on Feb. 7, 2013, the entire contents of which are incorporated herein by reference.

TECHNICAL FIELD

The present specification relates to a heterocyclic compound and an organic light emitting device using the same.

BACKGROUND ART

An organic light emitting phenomenon is an example of converting a current into visible rays by an internal process of a specific organic molecule. The organic light emitting phenomenon is based on the following principle.

When an organic material layer is positioned between an anode and a cathode, if a voltage is applied between two electrodes, electrons and holes are injected from the cathode and the anode into the organic material layer. The electrons and the holes injected into the organic material layer are recombined to form an exciton, and the exciton is reduced again to a bottom state to emit light. In general, an organic light emitting device using this principle may be constituted by a cathode, an anode, and an organic material layer positioned therebetween, for example, an organic material layer including a hole injection layer, a hole transport layer, a light emitting layer, and an electron transport layer.

A material used in the organic light emitting device is mostly a pure organic material or a complex compound where an organic material and metal form a complex, and may be classified into a hole injection material, a hole transport material, a light emitting material, an electron transport material, an electron injection material, and the like according to the purpose thereof. Herein, an organic material having a p-type property, that is, an organic material that is easily oxidized and has an electrochemically stable state during oxidation, is mostly used as the hole injection material or the hole transport material. Meanwhile, an organic material having an n-type property, that is, an organic material that is easily reduced and has an electrochemically stable state during reduction, is mostly used as the electron injection material or the electron transport material. A material having both p-type and n-type properties, that is, a material having a stable form in both oxidation and reduction states, may be used as the light emitting layer material, and a material having high light emitting efficiency for conversion of the exciton into light when the exciton is formed is preferable.

Accordingly, there is a demand to develop a novel organic material in the art.

SUMMARY OF THE INVENTION

The present specification has been made in an effort to provide a heterocyclic compound and an organic light emitting device using the same.

An exemplary embodiment of the present specification provides a compound represented by the following Chemical Formula 1 or 2.

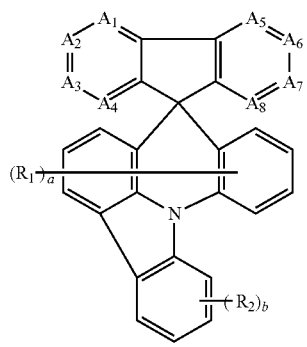

[Chemical Formula 1]

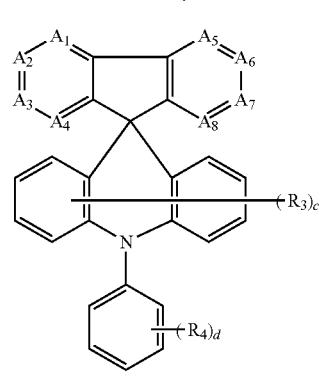

[Chemical Formula 2]

wherein a is an integer of 0 to 7,
b is an integer of 0 to 4,
c is an integer of 0 to 8,
d is an integer of 0 to 5,
$A_1$ to $A_8$ are the same as or different from each other and are each independently CR or N, but two or more of $A_1$ to $A_8$ are N, and R and $R_1$ to $R_4$ are the same as or different from each other, and are each independently hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted arylphosphine group; a substituted or unsubstituted phosphine oxide group; a substituted or unsubstituted aryl group; or a substituted or unsubstituted heterocyclic group including one or more of N, O, and S atoms.

Another exemplary embodiment of the present specification provides an organic light emitting device including: a first electrode, a second electrode, and organic material layers of one or more layers disposed between the first electrode and the second electrode, in which one or more layers of the organic material layers include the heterocyclic compound represented by Chemical Formula 1 or 2 or a compound in which a heat-curable or photo-curable functional group is introduced into the heterocyclic compound.

The heterocyclic compound according to the exemplary embodiment of the present specification has an appropriate energy level and excellent electrochemical stability and thermal stability. Accordingly, an organic light emitting device including the compound provides high efficiency and/or high driving stability.

DETAILED DESCRIPTION

Figure 1:
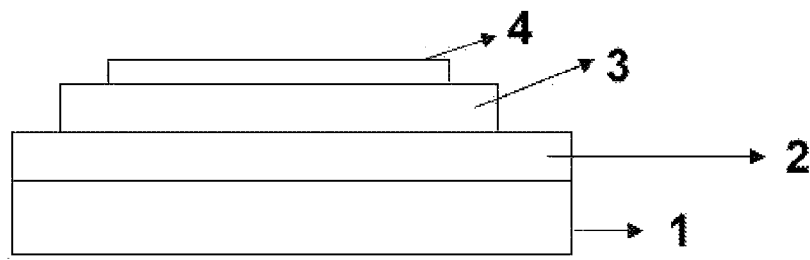
FIG. 1 illustrates an example of an organic light emitting device including a substrate 1, an anode 2, a light emitting layer 3, and a cathode 4.

Hereinafter, the present invention will be described in detail.

In an exemplary embodiment of the present specification, there is provided a compound represented by Chemical Formula 1.

In the exemplary embodiment of the present specification, there is provided a compound represented by Chemical Formula 2.

An organic light emitting device including the heterocyclic compound according to the exemplary embodiment of the present specification may have an effect of a driving voltage reduction and/or an efficiency increase.

Examples of substituent groups will be described below, but are not limited thereto.

In the present specification, examples of a halogen group include fluorine, chlorine, bromine, or iodine.

In the present specification, oxygen of an ester group may be substituted with a straight-chained, branched-chained, or cyclic-chained alkyl group having 1 to 25 carbon atoms, or an aryl group having 6 to 25 carbon atoms. Specifically, the ester group may be compounds having the following Structural Formulas, but is not limited thereto.

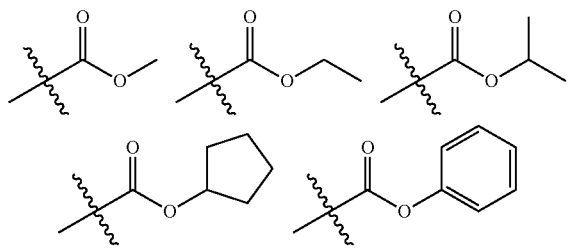

In the present specification, the number of carbon atoms of an imide group is not particularly limited but is preferably 1 to 25. Specifically, the imide group may be compounds having the following structures, but is not limited thereto.

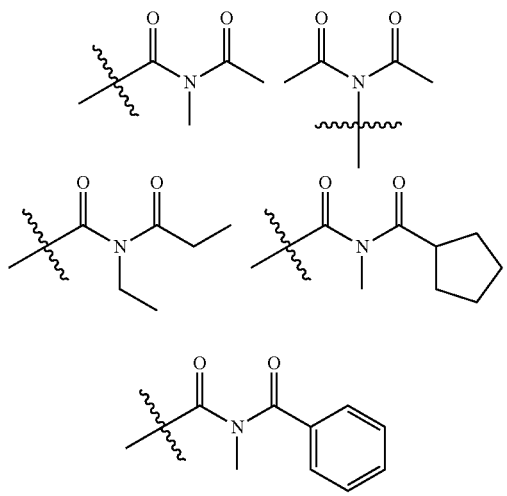

In the present specification, one or two nitrogen atoms of an amide group may be substituted with hydrogen, a straight-chained, branched-chained, or cyclic-chained alkyl group having 1 to 25 carbon atoms, or an aryl group having 6 to 25 carbon atoms. Specifically, the amide group may be compounds having the following Structural Formulas, but is not limited thereto.

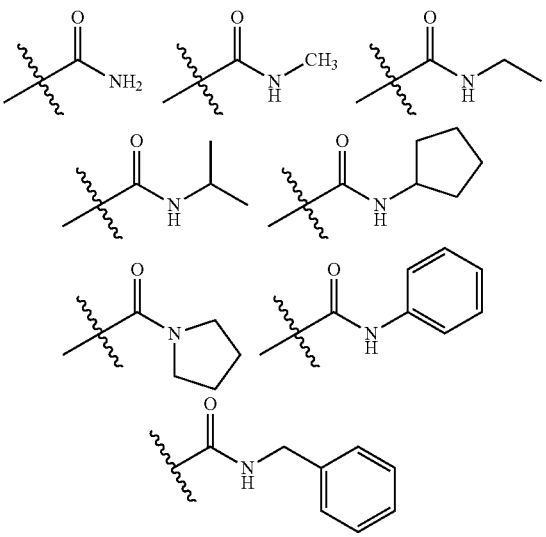

In the present specification, the alkyl group may be a straight or branched chain, and the number of carbon atoms thereof is not particularly limited but is preferably 1 to 50. Specific examples thereof include methyl, ethyl, propyl, n-propyl, isopropyl, butyl, n-butyl, isobutyl, tert-butyl, sec-butyl, 1-methyl-butyl, 1-ethyl-butyl, pentyl, n-pentyl, isopentyl, neopentyl, tert-pentyl, hexyl, n-hexyl, 1-methylpentyl, 2-methylpentyl, 4-methyl-2-pentyl, 3,3-dimethylbutyl, 2-ethylbutyl, heptyl, n-heptyl, 1-methylhexyl, cyclopentylmethyl, cyclohexylmethyl, octyl, n-octyl, tert-octyl, 1-methylheptyl, 2-ethylhexyl, 2-propylpentyl, n-nonyl, 2,2-dimethylheptyl, 1-ethyl-propyl, 1,1-dimethyl-propyl, isohexyl, 2-methylpentyl, 4-methylhexyl, 5-methylhexyl, and the like, but are not limited thereto.

In the present specification, a cycloalkyl group is not particularly limited, but the number of carbon atoms thereof is preferably 3 to 60, and the cycloalkyl group may have a monocycle or a polycycle. Specific examples thereof include cyclopropyl, cyclobutyl, cyclopentyl, 3-methylcyclopentyl, 2,3-dimethylcyclopentyl, cyclohexyl, 3-methylcyclohexyl, 4-methylcyclohexyl, 2,3-dimethylcyclohexyl, 3,4,5-trimethylcyclohexyl, 4-tert-butylcyclohexyl, cycloheptyl, cyclooctyl, and the like, but are not limited thereto.

In the present specification, the alkoxy group may be a straight, branched, or cyclic chain. The number of carbon atoms of the alkoxy group is not particularly limited, but preferably 1 to 20. Specific examples thereof may include methoxy, ethoxy, n-propoxy, isopropoxy, i-propyloxy, n-butoxy, isobutoxy, tert-butoxy, sec-butoxy, n-pentyloxy, neopentyloxy, isopentyloxy, n-hexyloxy, 3,3-dimethylbutyloxy, 2-ethylbutyloxy, n-octyloxy, n-nonyloxy, n-decyloxy, benzyloxy, p-methylbenzyloxy, and the like, but are not limited thereto.

In the present specification, the aryl group is an organic radical derived from aromatic hydrocarbons by removing one hydrogen, and may have a monocycle or a polycycle. The number of carbon atoms of the aryl group is not particularly limited, but preferably 6 to 60. Specific examples of the aryl group include monocyclic aromatics such as a phenyl group, a biphenyl group, a triphenyl group, a terphenyl group, and a stilbene group, polycyclic aromatics such as a naphthyl group, an anthracenyl group, a phenanthrenyl group, a pyrenyl group, a perylenyl group, a tetracenyl group, a chrysenyl group, a fluorenyl group, an acenaphthacenyl group, a triphenylene group, and a fluoranthene group, and the like, but are not limited thereto.

In the present specification, the fluorenyl group has a structure where two cyclic organic compounds are connected through one atom, and examples thereof include

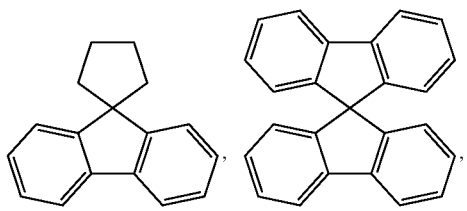

and the like.

In the present specification, the fluorenyl group includes a structure of an opened fluorenyl group, herein, the opened fluorenyl group has a structure where two cyclic compounds are connected through one atom and connection of one cyclic compound is broken, and examples thereof include

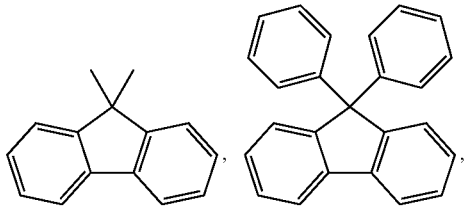

and the like.

In the present specification, the heterocyclic group is a heterocyclic group including O, N, or S as a heteroatom, and the number of carbon atoms thereof is not particularly limited, but is preferably 2 to 60. Examples of the heterocyclic group include a thiophene group, a furan group, a pyrrole group, an imidazole group, a thiazole group, an oxazol group, an oxadiazol group, a triazol group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzoimidazole group, a benzothiazol group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

In the present specification, the aryl group of an aryloxy group, an arylthioxy group, an arylsulfoxy group, and an aralkylamine group is the same as the aforementioned examples of the aryl group. Specific examples of the aryloxy group include phenoxy, p-tolyloxy, m-tolyloxy, 3,5-dimethyl-phenoxy, 2,4,6-trimethylphenoxy, p-tert-butylphenoxy, 3-biphenyloxy, 4-biphenyloxy, 1-naphthyloxy, 2-naphthyloxy, 4-methyl-1-naphthyloxy, 5-methyl-2-naphthyloxy, 1-anthryloxy, 2-anthryloxy, 9-anthryloxy, 1-phenanthryloxy, 3-phenanthryloxy, 9-phenanthryloxy, and the like, specific examples of the arylthioxy group include a phenylthioxy group, a 2-methylphenylthioxy group, a 4-tert-butylphenylthioxy group, and the like, and specific examples of the arylsulfoxy group include a benzenesulfoxy group, a p-toluenesulfoxy group, and the like, but the examples are not limited thereto.

In the present specification, the alkyl group of an alkylthioxy group and an alkylsulfoxy group is the same as the aforementioned examples of the alkyl group. Specific examples of the alkylthioxy group include a methylthioxy group, an ethylthioxy group, a tert-butylthioxy group, a hexylthioxy group, an octylthioxy group, and the like, and specific examples of the alkylsulfoxy group include mesyl, an ethylsulfoxy group, a propylsulfoxy group, a butylsulfoxy group, and the like, but the examples are not limited thereto.

In the present specification, a heteroaryl group of a heteroarylamine group may be selected from the aforementioned examples of the heterocyclic group.

In the present specification, specific examples of an aralkyl group of the aralkylamine group include a benzyl group, a p-methylbenzyl group, an m-methylbenzyl group, a p-ethylbenzyl group, an m-ethylbenzyl group, a 3,5-dimethylbenzyl group, an α-methylbenzyl group, an α,α-dimethylbenzyl group, an α,α-methylphenylbenzyl group, a 1-naphthylbenzyl group, a 2-naphthylbenzyl group, a p-fluorobenzyl group, a 3,5-difluorobenzyl group, an α,α-ditrifluoromethylbenzyl group, a p-methoxybenzyl group, an m-methoxybenzyl group, an α-phenoxybenzyl group, an α-benzyloxybenzyl group, a naphthylmethyl group, a naphthylethyl group, a naphthylisopropyl group, a pyrrolylmethyl group, a pyrrolelethyl group, an aminobenzyl group, a nitrobenzyl group, a cyanobenzyl group, a 1-hydroxy-2-phenylisopropyl group, a 1-chloro-2-phenylisopropyl group, and the like, but are not limited thereto.

In the present specification, the alkenyl group may be a straight or branched chain, and the number of carbon atoms thereof is not particularly limited but is preferably 2 to 40. Specific examples thereof include vinyl, 1-prophenyl, isoprophenyl, 1-butenyl, 2-butenyl, 3-butenyl, 1-pentenyl, 2-pentenyl, 3-pentenyl, 3-methyl-1-butenyl, 1,3-butadienyl, allyl, 1-phenylvinyl-1-yl, 2-phenylvinyl-1-yl, 2,2-diphenylvinyl-1-yl, 2-phenyl-2-(naphthyl-1-yl)vinyl-1-yl, 2,2-bis (diphenyl-1-yl)vinyl-1-yl, a stilbenyl group, a styrenyl group, and the like, but are not limited thereto.

In the present specification, specific examples of the silyl group include a trimethylsilyl group, a triethylsilyl group, a t-butyldimethylsilyl group, a vinyldimethylsilyl group, a propyldimethylsilyl group, a triphenylsilyl group, a diphenylsilyl group, a phenylsilyl group, and the like, but are not limited thereto.

In the present specification, the number of carbon atoms of an amine group is not particularly limited, but preferably 1 to 30. Specific examples of the amine group include a methylamine group, a dimethylamine group, an ethylamine group, a diethylamine group, a phenylamine group, a naphthylamine group, a biphenylamine group, an anthracenylamine group, a 9-methyl-anthracenylamine group, a diphenylamine group, a phenylnaphthylamine group, a ditolylamine group, a phenyltolylamine group, a triphenylamine group, and the like, but are not limited thereto.

In the present specification, examples of an arylamine group include a substituted or unsubstituted monoarylamine group, a substituted or unsubstituted diarylamine group, or a substituted or unsubstituted triarylamine group. The aryl group of the arylamine group may be a monocyclic aryl group or a polycyclic aryl group. The arylamine group including two or more aryl groups may include the monocyclic aryl group, the polycyclic aryl group, or both the monocyclic aryl group and the polycyclic aryl group.

Specific examples of the arylamine group include phenylamine, naphthylamine, biphenylamine, anthracenylamine, 3-methyl-phenylamine, 4-methyl-naphthylamine, 2-methyl-biphenylamine, 9-methyl-anthracenylamine, a diphenylamine group, a phenylnaphthylamine group, a ditolylamine group, a phenyltolylamine group, carbazole, a triphenylamine group, and the like, but are not limited thereto.

In the present specification, examples of an arylphosphine group include a substituted or unsubstituted monoarylphosphine group, a substituted or unsubstituted diarylphosphine group, or a substituted or unsubstituted triarylphosphine group. The aryl group of the arylphosphine group may be a monocyclic aryl group or a polycyclic aryl group. The arylphosphine group including two or more aryl groups may include the monocyclic aryl group, the polycyclic aryl group, or both the monocyclic aryl group and the polycyclic aryl group.

Further, in the present specification, the term "substituted or unsubstituted" means that substitution is performed by one or more substituent groups selected from the group consisting of deuterium; a halogen group; an alkyl group; an alkenyl group; an alkoxy group; a cycloalkyl group; a silyl group; an arylalkenyl group; an aryl group; an aryloxy group; an alkylthioxy group; an alkylsulfoxy group; an arylsulfoxy group; a boron group; an alkylamine group; an aralkylamine group; an arylamine group; a heteroaryl group; a carbazole group; an arylamine group; an aryl group; a fluorenyl group; a nitrile group; a nitro group; a hydroxy group; and a heterocyclic group including one or more of N, O, and S atoms, or there is no substituent group, and the substituent groups may be further substituted or unsubstituted.

The term "substituted" means that a hydrogen atom bonded to a carbon atom of a compound is changed into another substituent group, a substitution position is not limited as long as the substitution position is a position at which the hydrogen atom is substituted, that is, a position at which the substituent group can be substituted, and in the case where two or more atoms are substituted, two or more substituent groups may be the same as or different from each other.

In the exemplary embodiment of the present specification, at least two of $A_1$ to $A_8$ are N.

In the exemplary embodiment of the present specification, at least one of $A_1$ to $A_4$ is N.

In the exemplary embodiment of the present specification, at least two of $A_1$ to $A_4$ are N.

In the exemplary embodiment of the present specification, at least one of $A_5$ to $A_8$ is N.

In the exemplary embodiment of the present specification, at least two of $A_5$ to $A_8$ are N.

In the exemplary embodiment of the present specification, $A_5$ is N.

In the exemplary embodiment of the present specification, $A_6$ is N.

In the exemplary embodiment of the present specification, $A_7$ is N.

In the exemplary embodiment of the present specification, $A_8$ is N.

In the exemplary embodiment of the present specification, $A_5$ and $A_7$ are N.

In the exemplary embodiment of the present specification, $A_6$ and $A_8$ are N.

In the exemplary embodiment of the present specification, $A_5$ is CR.

In the exemplary embodiment of the present specification, $A_6$ is CR.

In the exemplary embodiment of the present specification, $A_7$ is CR.

In the exemplary embodiment of the present specification, $A_8$ is CR.

In the exemplary embodiment of the present specification, $A_5$ and $A_7$ are N, $A_6$ and $A_8$ are CR or $A_6$ and $A_8$ are N, and $A_5$ and $A_7$ are CR.

In the exemplary embodiment of the present specification, $A_5$ and $A_7$ are N and $A_6$ is CR.

In the exemplary embodiment of the present specification, $A_5$ and $A_7$ are N, $A_6$ is CR, and $A_8$ is CR.

In the exemplary embodiment of the present specification, $A_6$ and $A_8$ are N and $A_7$ is CR.

In the exemplary embodiment of the present specification, $A_6$ and $A_8$ are N, $A_7$ is CR, and $A_5$ is CH.

In the exemplary embodiment of the present specification, $A_6$ and $A_8$ are N, $A_7$ is CR, and $A_5$ is CR.

In the exemplary embodiment of the present specification, R is hydrogen; a substituted or unsubstituted aryl group; or a substituted or unsubstituted heterocyclic group including one or more of substituted or unsubstituted N, O, and S atoms.

In another exemplary embodiment, R is hydrogen; an aryl group unsubstituted or substituted with one or two or more substituent groups selected from the group consisting of a substituted or unsubstituted phosphine oxide group, a substituted or unsubstituted aryl group, and a substituted or unsubstituted heterocyclic group including one or more of N, O, and S atoms; or a heterocyclic group including one or more of N, O, and S atoms unsubstituted or substituted with one or two or more substituent groups selected from the group consisting of a substituted or unsubstituted phosphine oxide group, a substituted or unsubstituted aryl group, and a substituted or unsubstituted heterocyclic group including one or more of N, O, and S atoms.

In the exemplary embodiment of the present specification, R is hydrogen; a phenyl group unsubstituted or substituted with a substituent group selected from the group consisting of a phenyl group, a phosphine oxide group substituted with a phenyl group, a triazine group, and a pyrimidine group; a naphthyl group unsubstituted or substituted with a substituent group selected from the group consisting of a phenyl group, a phosphine oxide group substituted with a phenyl group, a triazine group, and a pyrimidine group; a biphenyl group unsubstituted or substituted with a substituent group selected from the group consisting of a phenyl group, a phosphine oxide group substituted with a phenyl group, a triazine group, and a pyrimidine group; or a pyridine group unsubstituted or substituted with a substituent group selected from the group consisting of a phenyl group, a phosphine oxide group substituted with a phenyl group, a triazine group, and a pyrimidine group.

In the exemplary embodiment of the present specification, R is hydrogen; a phenyl group unsubstituted or substituted with a substituent group selected from the group consisting of a phenyl group, a phosphine oxide group substituted with a phenyl group, a triazine group, and a pyrimidine group; a naphthyl group; a biphenyl group unsubstituted or substituted with a phosphine oxide group substituted with a phenyl group; or a pyridine group.

In the exemplary embodiment of the present specification, R is hydrogen.

In the exemplary embodiment of the present specification, R is a substituted or unsubstituted aryl group.

In the exemplary embodiment of the present specification, R is a substituted or unsubstituted phenyl group.

In the exemplary embodiment of the present specification, R is a phenyl group.

In the exemplary embodiment of the present specification, R is a phenyl group substituted with a substituted or unsubstituted aryl group.

In the exemplary embodiment of the present specification, R is a phenyl group unsubstituted or substituted with a phenyl group.

In the exemplary embodiment of the present specification, R is a phenyl group substituted with a substituted or unsubstituted phosphine oxide group.

In another exemplary embodiment, R is a phenyl group substituted with a phosphine oxide group substituted with an aryl group.

In the exemplary embodiment of the present specification, R is a phenyl group substituted with a phosphine oxide group substituted with a phenyl group.

In the exemplary embodiment of the present specification, R is a phenyl group substituted with a substituted or unsubstituted heterocyclic group including one or more of N, O, and S atoms.

In another exemplary embodiment, R is a phenyl group substituted with a substituted or unsubstituted heterocyclic group including N.

In one exemplary embodiment, R is a phenyl group substituted with a substituted or unsubstituted triazine group.

In another exemplary embodiment, R is a phenyl group substituted with a triazine group substituted with a phenyl group.

In the exemplary embodiment of the present specification, R is a phenyl group substituted with a substituted or unsubstituted pyrimidine group.

In another exemplary embodiment, R is a phenyl group substituted with a pyrimidine group unsubstituted or substituted with a phenyl group.

In the exemplary embodiment of the present specification, the pyrimidine group is

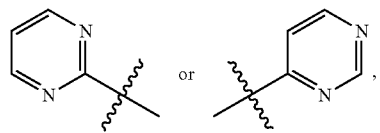 [SMILES: *c1ncccn1 ; *c1ccncn1]

and may be unsubstituted or substituted with an additional substituent group.

In the exemplary embodiment of the present specification, R is a substituted or unsubstituted naphthyl group.

In another exemplary embodiment, R is a naphthyl group.

In another exemplary embodiment, R is a substituted or unsubstituted biphenyl group.

In another exemplary embodiment, R is a biphenyl group.

In the exemplary embodiment of the present specification, R is a biphenyl group substituted with a substituted or unsubstituted phosphine oxide group.

In another exemplary embodiment, R is a biphenyl group substituted with a phosphine oxide group substituted with an aryl group.

In the exemplary embodiment of the present specification, R is a biphenyl group substituted with a phosphine oxide group substituted with a phenyl group.

In the exemplary embodiment of the present specification, R is a substituted or unsubstituted heterocyclic group including one or more of N, O, and S atoms.

In another exemplary embodiment, R is a substituted or unsubstituted heterocyclic group including one or more N atoms.

In another exemplary embodiment, R is a substituted or unsubstituted pyridine group.

In the exemplary embodiment of the present specification, the pyridine group is

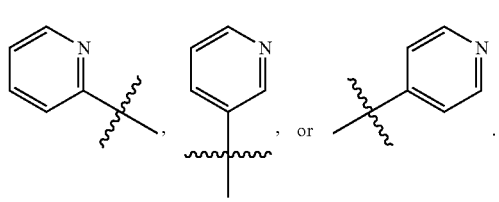 [SMILES: *c1ccccn1 ; *c1cccnc1 ; *c1ccncc1]

In the exemplary embodiment of the present specification, $R_1$ is hydrogen.

In another exemplary embodiment, $R_2$ is hydrogen.

In one exemplary embodiment, $R_3$ is hydrogen.

In another exemplary embodiment, $R_4$ is hydrogen.

In the exemplary embodiment of the present specification, the heterocyclic compound represented by Chemical Formula 1 is represented by any one of the following Chemical Formulas 1-1 to 1-36.

Chemical Formula 1-1
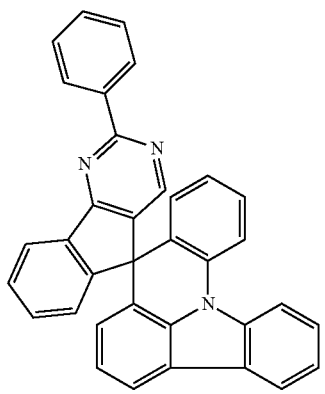
Chemical Formula 1-2
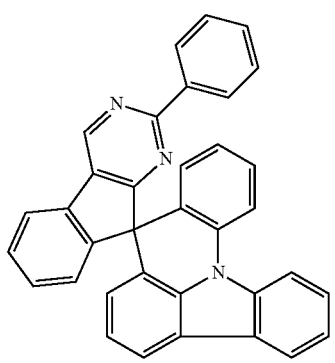
Chemical Formula 1-3
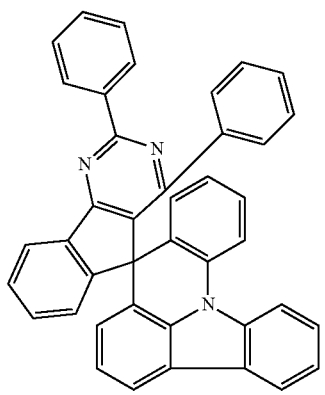
Chemical Formula 1-4
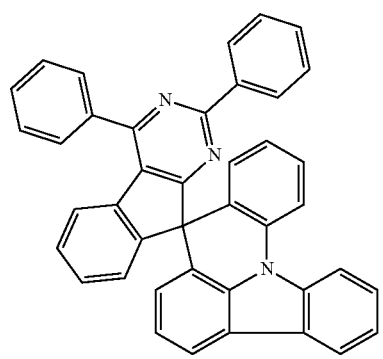
Chemical Formula 1-5
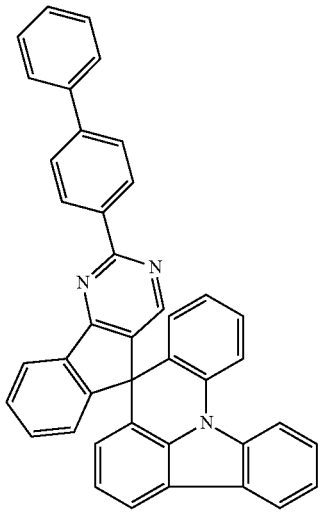
Chemical Formula 1-6
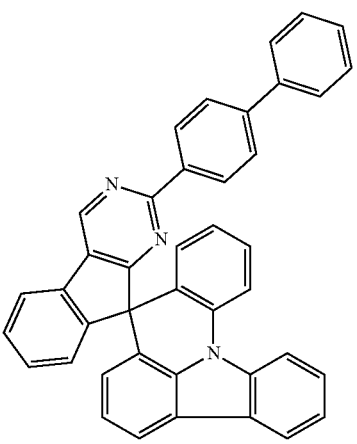
Chemical Formula 1-7
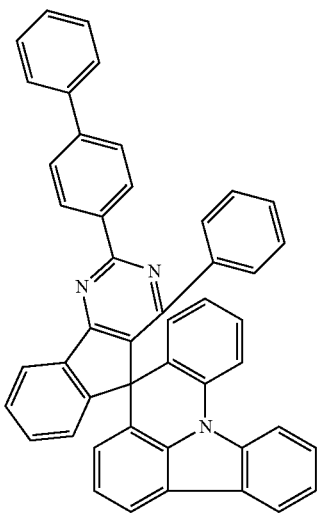

Chemical Formula 1-8
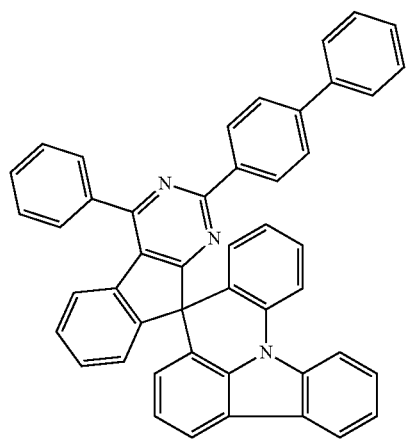
Chemical Formula 1-9
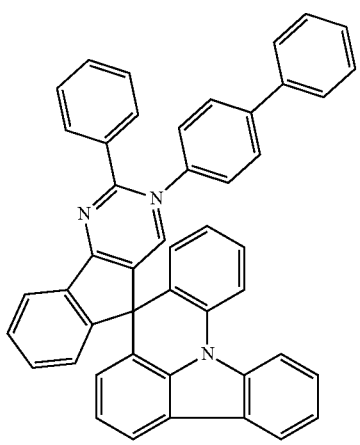
Chemical Formula 1-10
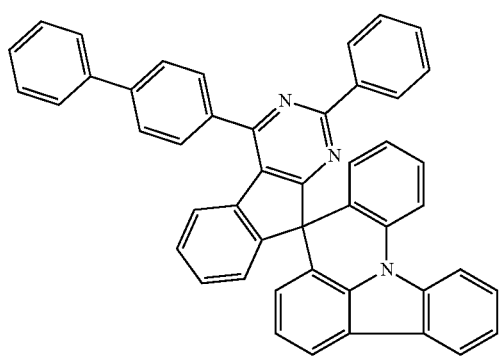
Chemical Formula 1-11
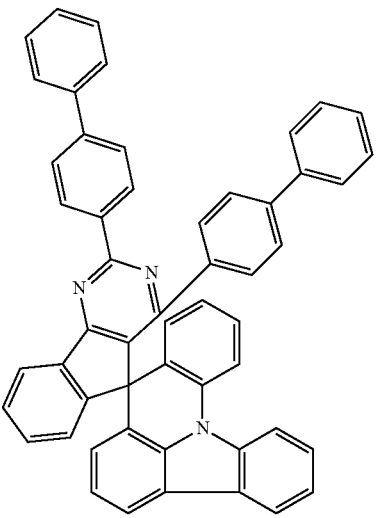
Chemical Formula 1-12
Chemical Formula 1-13
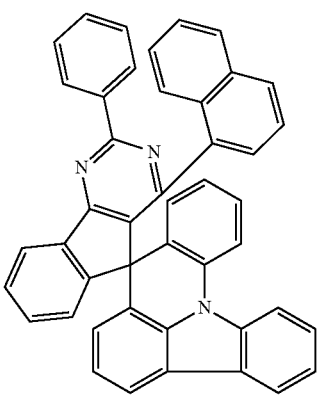

Chemical Formula 1-14
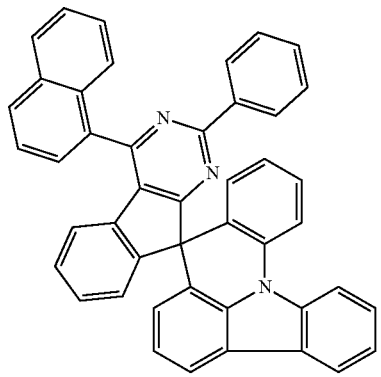
Chemical Formula 1-15
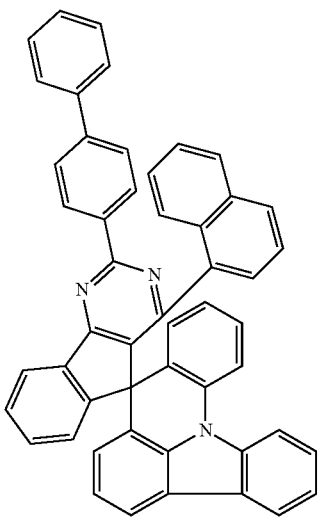
Chemical Formula 1-16
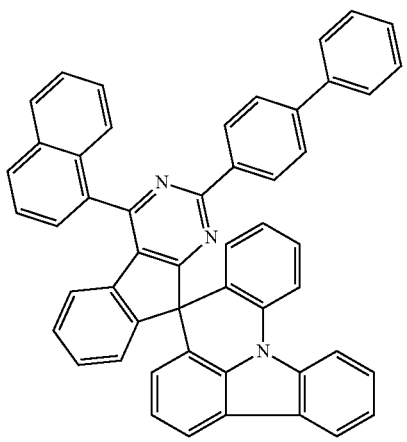
Chemical Formula 1-17
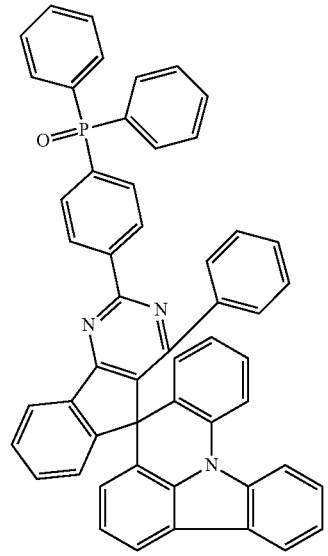
Chemical Formula 1-18
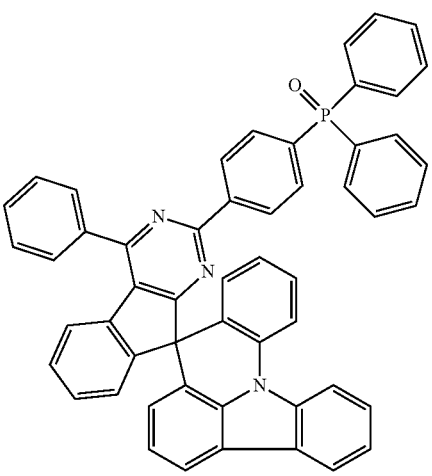
Chemical Formula 1-19
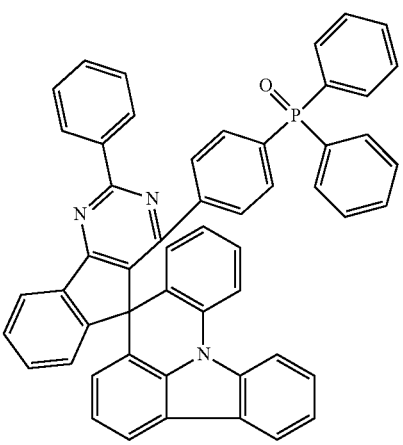

-continued
Chemical Formula 1-20
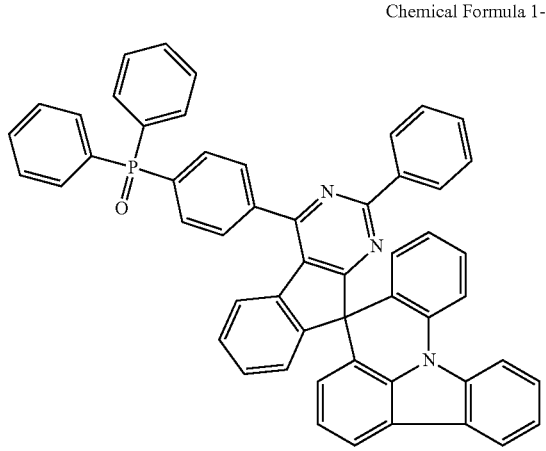
Chemical Formula 1-21
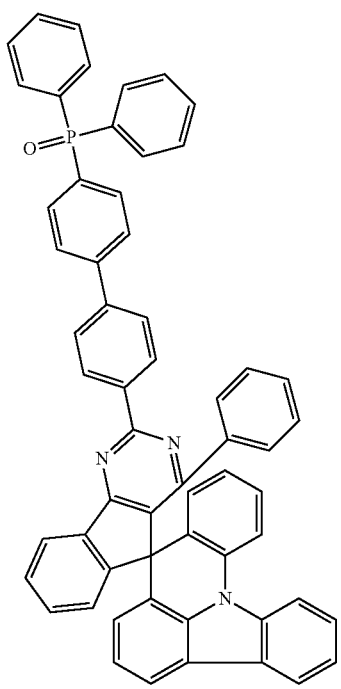
Chemical Formula 1-22
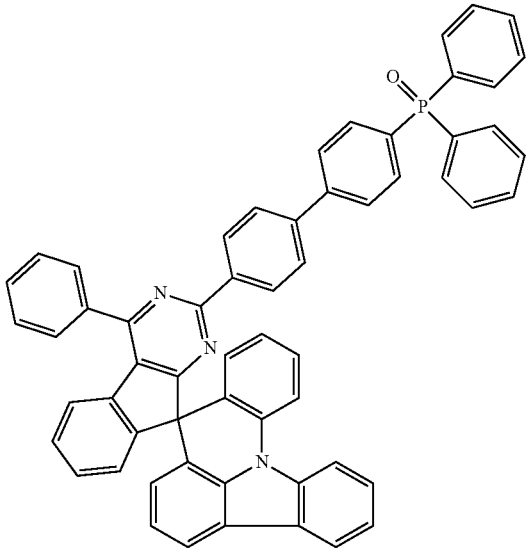
Chemical Formula 1-23
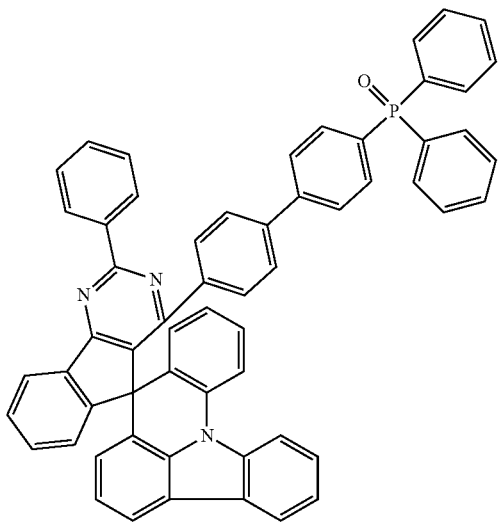
Chemical Formula 1-24
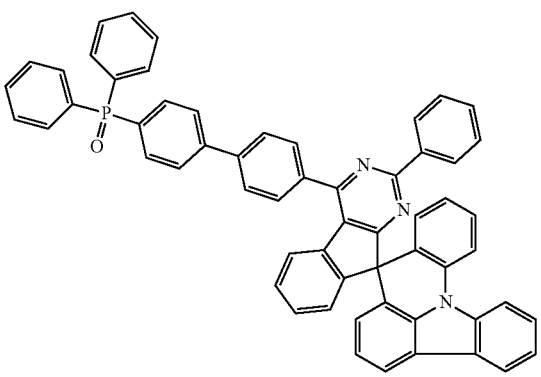

Chemical Formula 1-25
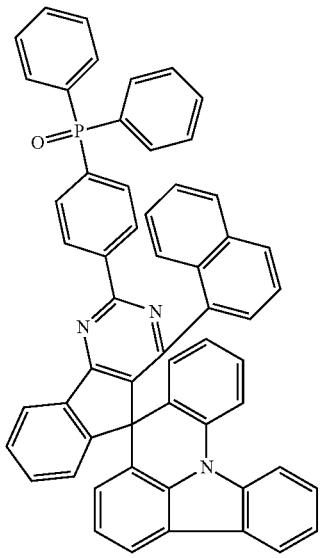
Chemical Formula 1-26
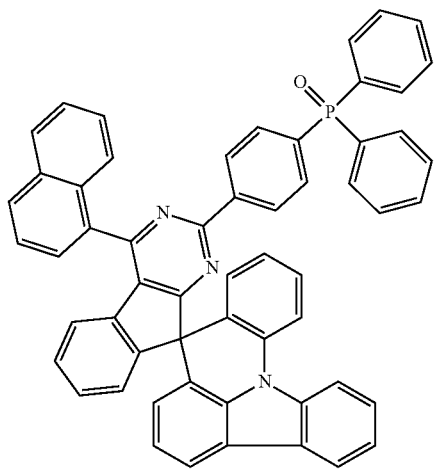
Chemical Formula 1-27
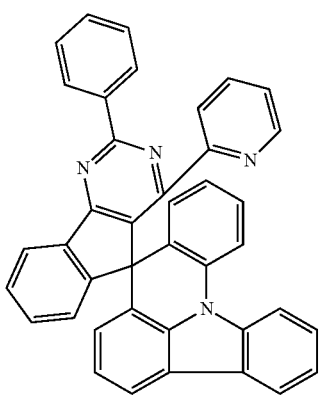
Chemical Formula 1-28
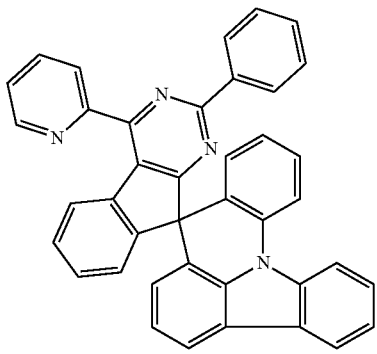
Chemical Formula 1-29
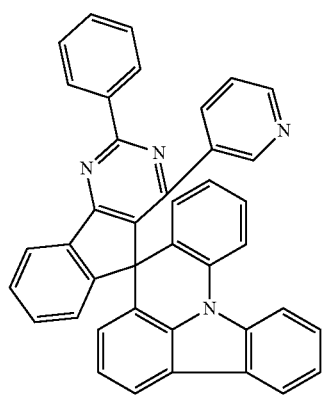
Chemical Formula 1-30
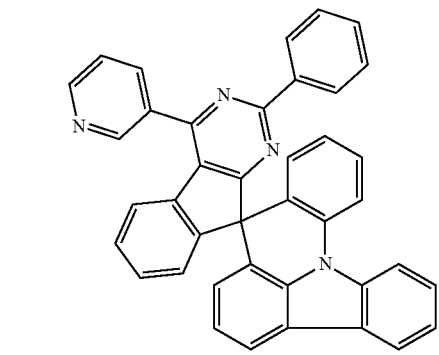
Chemical Formula 1-31
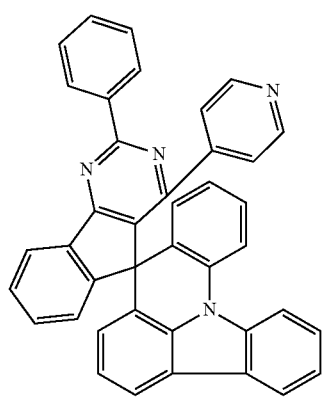

Chemical Formula 1-32
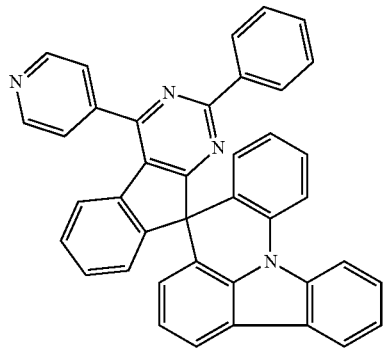
Chemical Formula 1-33
Chemical Formula 1-34
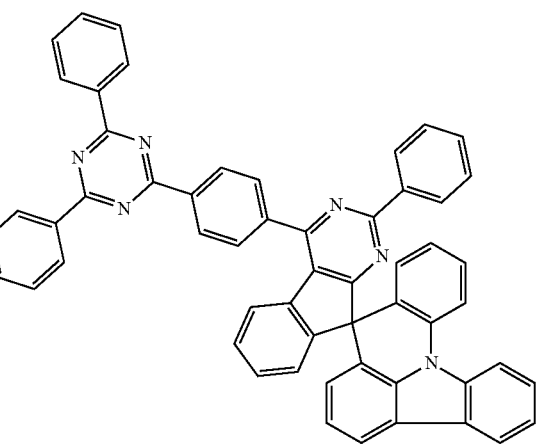
Chemical Formula 1-35
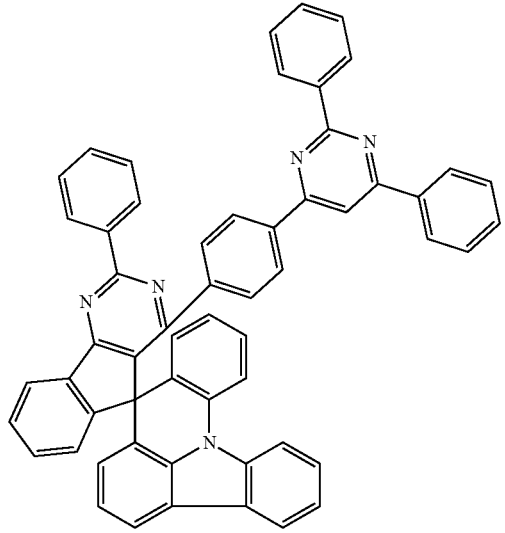
Chemical Formula 1-36
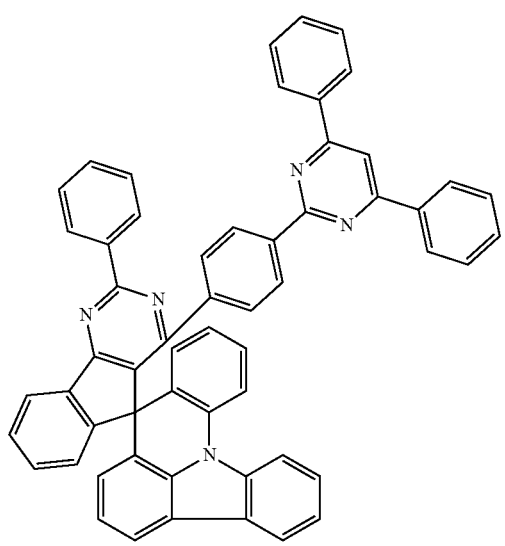
In the exemplary embodiment of the present specification, the heterocyclic compound represented by Chemical Formula 2 is represented by any one of the following Chemical Formulas 2-1 to 2-32.
Chemical Formula 2-1
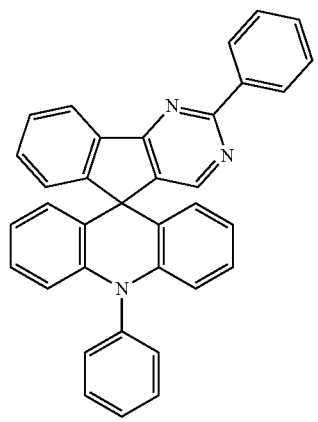

Chemical Formula 2-2
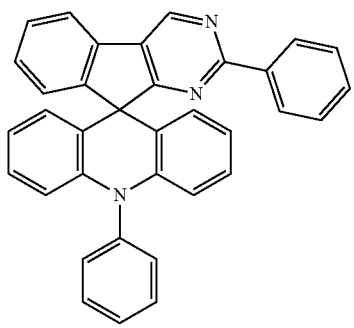
Chemical Formula 2-5
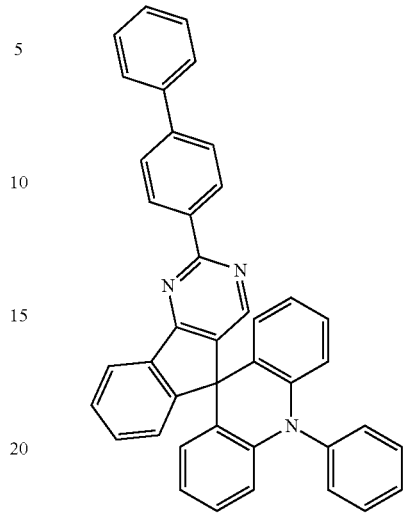
Chemical Formula 2-3
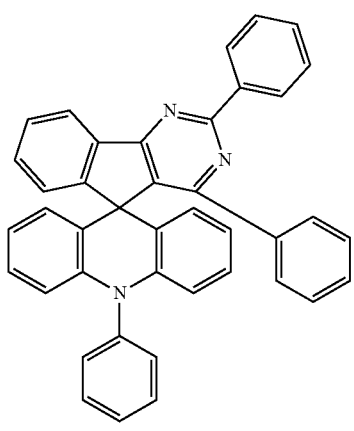
Chemical Formula 2-6
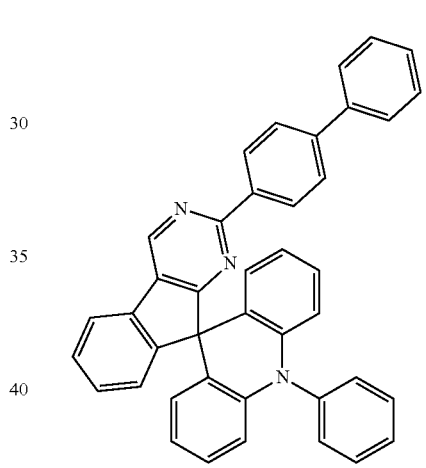
Chemical Formula 2-4
Chemical Formula 2-7
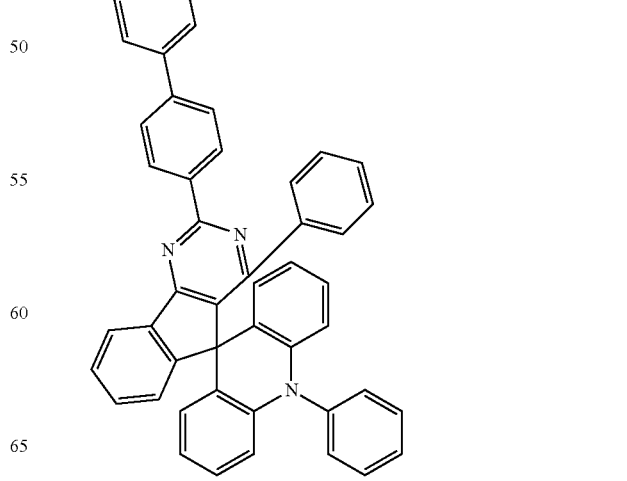

Chemical Formula 2-8
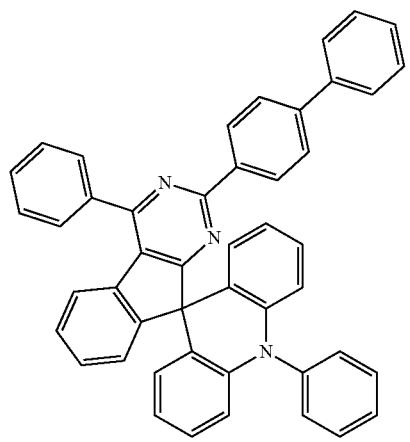
Chemical Formula 2-9
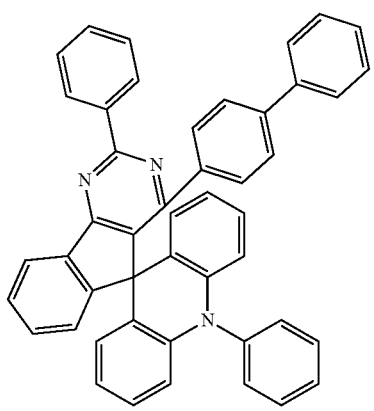
Chemical Formula 2-10
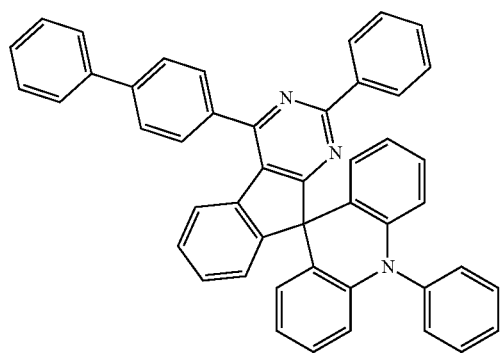
Chemical Formula 2-11
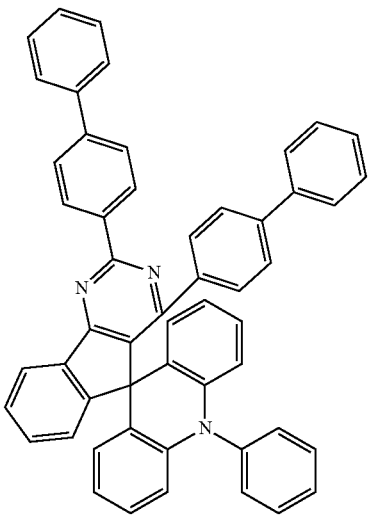
Chemical Formula 2-12
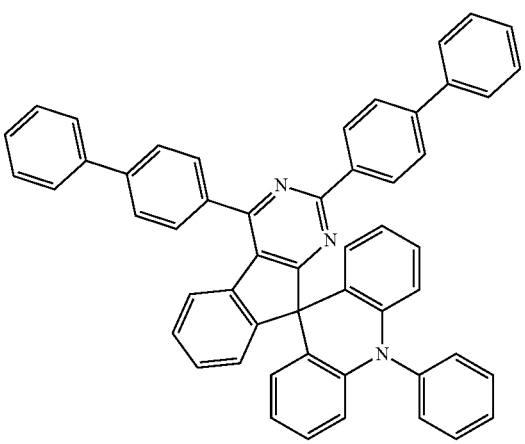
Chemical Formula 2-13
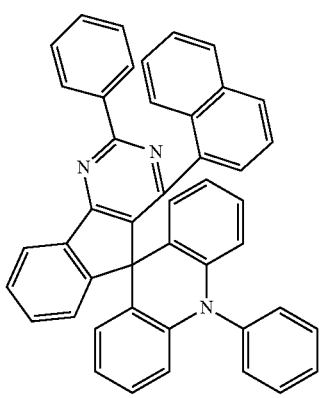

Chemical Formula 2-14
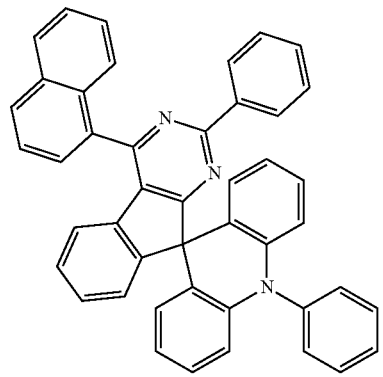
Chemical Formula 2-15
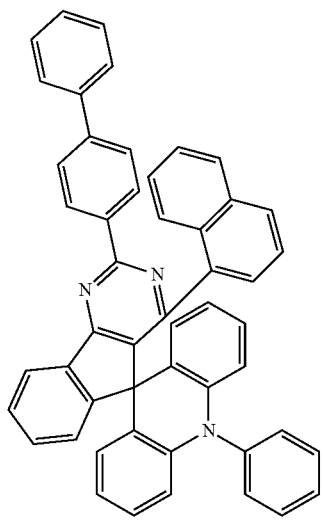
Chemical Formula 2-16
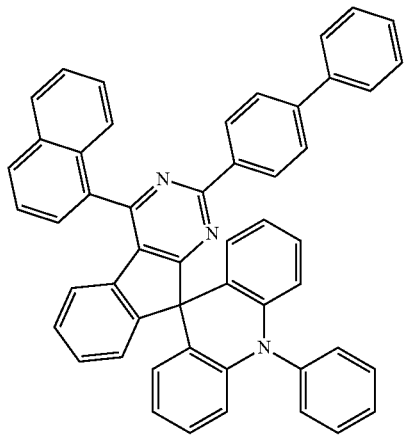
Chemical Formula 2-17
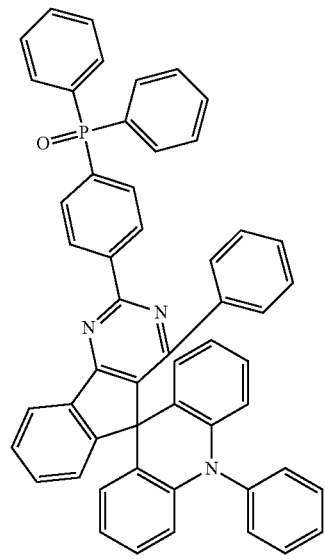
Chemical Formula 2-18
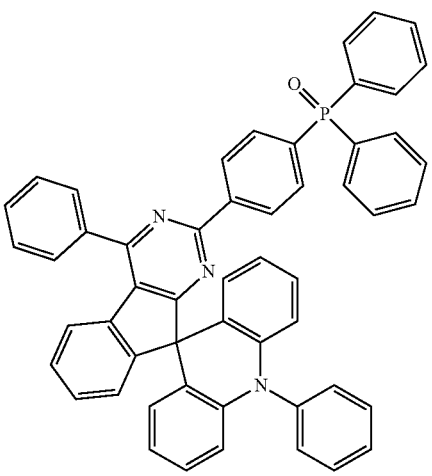
Chemical Formula 2-19
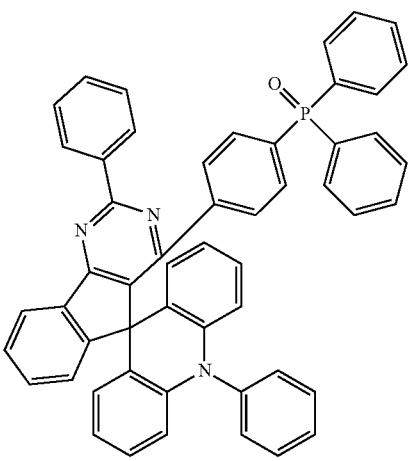

Chemical Formula 2-20
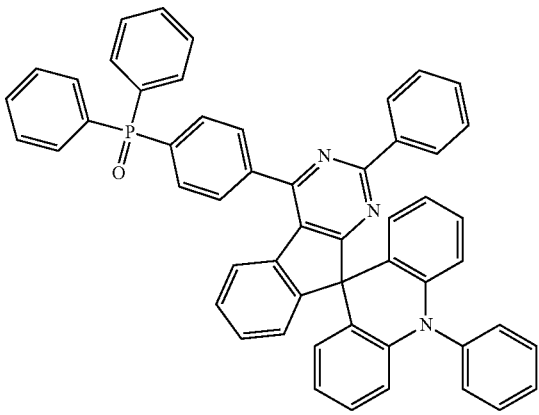
Chemical Formula 2-21
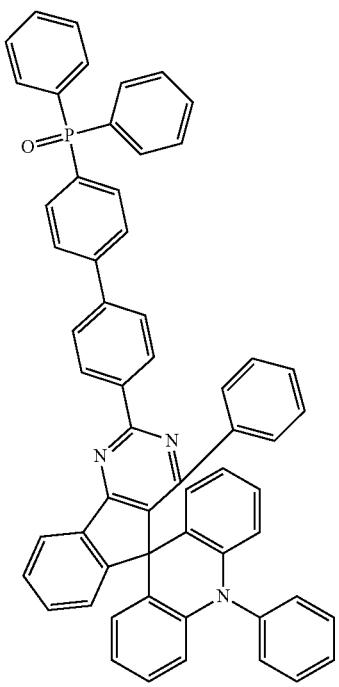
Chemical Formula 2-22
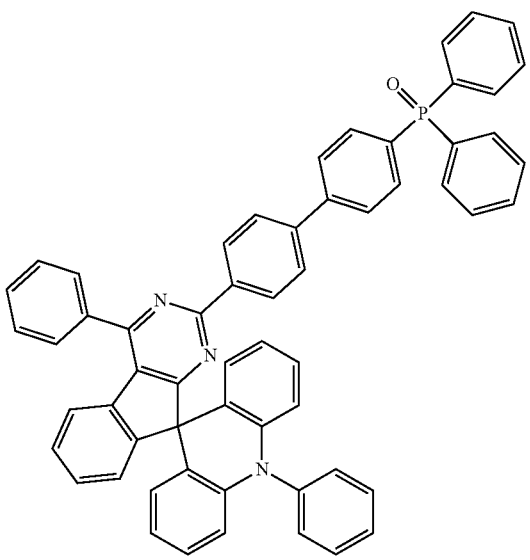
Chemical Formula 2-23
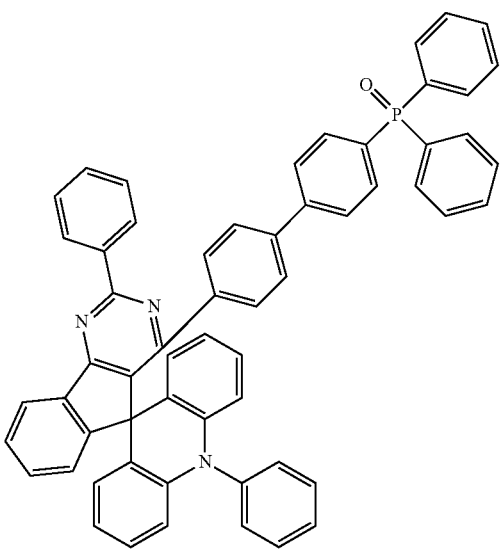
Chemical Formula 2-24
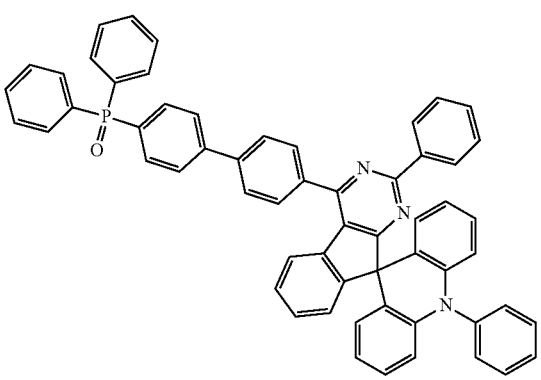

Chemical Formula 2-25
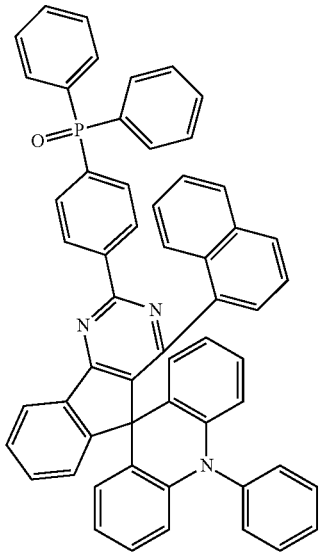
Chemical Formula 2-26
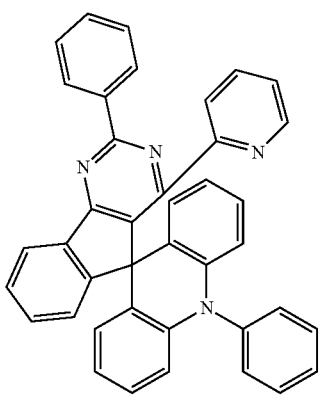
Chemical Formula 2-27
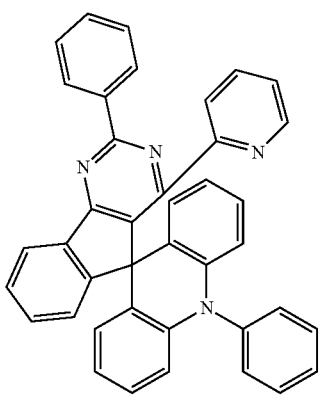
Chemical Formula 2-28
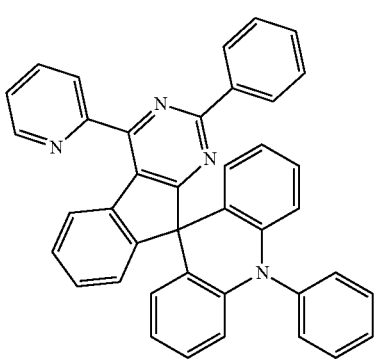
Chemical Formula 2-29
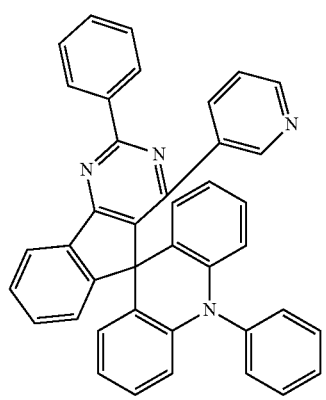
Chemical Formula 2-30
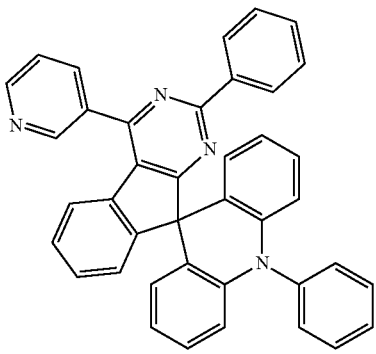
Chemical Formula 2-31
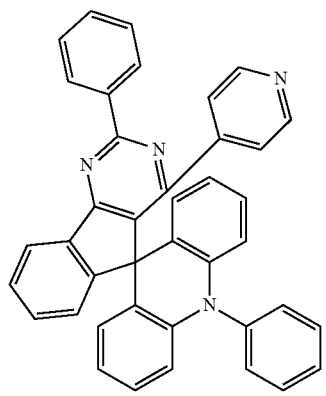

Chemical Formula 2-32

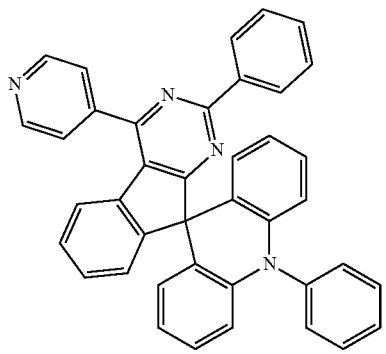

The heterocyclic compound of Chemical Formula 1 or 2 may be prepared based on Preparation Examples as will be described later.

In the exemplary embodiment of the present specification, the heterocyclic compound represented by Chemical Formula 1 as well as Chemical Formulas 1-1 to 1-36 may be prepared by reacting indeno pyrimidi-5-on substituted with R with 9-(2-bromophenyl)-carbazole and performing a ring-closing reaction.

In the exemplary embodiment of the present specification, the heterocyclic compound represented by Chemical Formula 2 as well as Chemical Formulas 2-1 to 2-32 may be prepared by reacting indeno pyrimidi-5-on substituted with R with 2-bromo-diphenylaniline and performing a ring-closing reaction.

In the exemplary embodiment of the present specification, the compound of Chemical Formula 1 or 2 includes a core structure in which heterocyclic groups obtained by condensation of two 3-membered cycles or condensation of a 3-membered cycle and a 5-membered cycle based on carbon are bonded in a spiro structure.

In the exemplary embodiment of the present specification, the compound of Chemical Formula 1 includes a core structure in which a substituted or unsubstituted indenopyrimidine group and a substituted or unsubstituted acrydine group are bonded in a spiro structure.

The compound of Chemical Formula 1 or 2 has a property suitable to be used as an organic material layer used in an organic light emitting device by introducing various substituents to the core structure represented in Chemical Formula 1 or Chemical Formula 2.

In the exemplary embodiment of the present specification, a core of the compound of Chemical Formula 1 or 2 limits conjugation between the heterocyclic groups in which the two 3-membered cycles are condensed or the 3-membered cycle and the 5-membered cycle are condensed based on carbon, which are subjected to spiro bonding.

A conjugation length of the compound has a close relationship with an energy band gap. Specifically, the energy band gap is reduced as the conjugation length of the compound increases. As described above, since the core of the compound of Chemical Formula 1 or Chemical Formula 2 includes a limited conjugation, the core has a property of a large energy band gap.

In the present specification, as described above, the compound having various energy band gaps may be synthesized by introducing various substituent groups to positions of R, and $R_1$ to $R_4$ of the core structure having the large energy band gap. Since the compound of Chemical Formula 1 or Chemical Formula 2 according to the exemplary embodiment of the present specification has the large energy band gap, it is easy to adjust the energy band gap by introducing the substituent group.

Further, in the present specification, HOMO and LUMO energy levels of the compound may be adjusted by introducing various substituent groups to the positions of R, and $R_1$ to $R_4$ of the core structure which is the same as that described above.

Accordingly, the organic light emitting device including the compound of Chemical Formula 1 or Chemical Formula 2 according to the exemplary embodiment of the present specification may provide an organic light emitting device having high efficiency and a long life-span.

Further, compounds having intrinsic properties of the introduced substituent groups may be synthesized by introducing various substituent groups to the core structure which is the same as that described above. For example, a material satisfying conditions required in each organic material layer may be synthesized by introducing the substituent group mainly used in a hole injection layer material, a hole transport material, a light emitting layer material, and an electron transport layer material used to manufacture the organic light emitting device to the core structure.

The heterocyclic compound of Chemical Formula 1 or Chemical Formula 2 according to the exemplary embodiment of the present specification has appropriate hole or electron mobility. Accordingly, in the case where the heterocyclic compound is applied to the organic light emitting device, densities of holes and electrons may be allowed to be balanced in a light emitting layer to maximize formation of excitons.

The heterocyclic compound of Chemical Formula 1 or Chemical Formula 2 according to the exemplary embodiment of the present specification has an excellent interfacial property with the adjacent layer, and thus has a merit in that stability of the device is high.

The heterocyclic compound of Chemical Formula 1 or Chemical Formula 2 according to the exemplary embodiment of the present specification has a high glass transition temperature ($T_g$), and thus has excellent thermal stability. Such an increase in thermal stability becomes an important factor providing driving stability to the device.

Further, the present specification provides an organic light emitting device using the compound of Chemical Formula 1 or Chemical Formula 2.

There is provided the organic light emitting device including a first electrode, a second electrode, and organic material layers formed of one or more layers including a light emitting layer disposed between the first electrode and the second electrode, in which one or more layers of the organic material layers include the heterocyclic compound or a compound in which a heat-curable or photo-curable functional group is introduced into the heterocyclic compound.

In the exemplary embodiment of the present specification, the organic material layer includes a hole transport layer, a hole injection layer, or a layer where both the hole transporting and the hole injection are performed, and the hole transport layer, the hole injection layer, or the layer where both hole transporting and hole injection are performed includes the heterocyclic compound or the compound in which the heat-curable or photo-curable functional group is introduced into the heterocyclic compound.

In the exemplary embodiment of the present specification, the light emitting layer includes the heterocyclic compound or the compound in which the heat-curable or photo-curable functional group is introduced into the heterocyclic compound.

In the exemplary embodiment of the present specification, the organic material layer includes the heterocyclic compound or the compound in which the heat-curable or photo-curable functional group is introduced into the heterocyclic compound as a host.

In the exemplary embodiment of the present specification, the organic material layer includes the heterocyclic compound or the compound in which the heat-curable or photo-curable functional group is introduced into the heterocyclic compound as the host, and another organic compound, a metal, or a metal compound as a dopant.

In the exemplary embodiment of the present specification, the organic material layer includes the light emitting layer, and the heterocyclic compound or the compound in which the heat-curable or photo-curable functional group is introduced into the heterocyclic compound as a host of the light emitting layer.

In another exemplary embodiment, the heterocyclic compound or the compound in which the heat-curable or photo-curable functional group is introduced into the heterocyclic compound is included as the host of the light emitting layer, and the organic compound, the metal, or the metal compound is included as the dopant.

In the exemplary embodiment of the present specification, the organic material layer includes an electron transport layer, and the electron transport layer includes the heterocyclic compound or the compound in which the heat-curable or photo-curable functional group is introduced into the heterocyclic compound.

In the exemplary embodiment of the present specification, the organic material layer includes an electron injection layer, and the electron injection layer includes the heterocyclic compound or the compound in which the heat-curable or photo-curable functional group is introduced into the heterocyclic compound.

In the exemplary embodiment of the present specification, the organic material layer includes the layer where both the electron injection and the electron transporting are performed, and the layer where both electron injection and electron transporting are performed includes the heterocyclic compound or the compound in which the heat-curable or photo-curable functional group is introduced into the heterocyclic compound.

In the exemplary embodiment of the present specification, the heterocyclic compound is included in the light emitting layer and/or the electron transport layer.

In the organic light emitting device of the present specification, the compound in which the heat-curable or photo-curable functional group is introduced into the compound of Chemical Formula 1 or Chemical Formula 2 may be used instead of the compound of Chemical Formula 1 or Chemical Formula 2. The compound may be formed into the organic material layer by a method of forming a thin film by a solution coating method and then curing the thin film when the device is manufactured while maintaining basic physical properties of the compound of Chemical Formula 1 or Chemical Formula 2.

In the exemplary embodiment of the present specification, the heat-curable or photo-curable functional group is a vinyl group or an acryl group.

In the exemplary embodiment of the present specification, the organic material layer further includes one layer or two or more layers selected from the group consisting of the hole injection layer, the hole transport layer, the electron transport layer, the electron injection layer, an electron blocking layer, and a hole blocking layer.

The organic material layer of the organic light emitting device of the present specification may have a single layer structure, or a multilayered structure in which two or more organic material layers are laminated. For example, the organic light emitting device of the present specification may have a structure including the hole injection layer, the hole transport layer, the light emitting layer, the electron transport layer, the electron injection layer, or the like as the organic material layer. However, the structure of the organic light emitting device is not limited thereto, but may include a smaller number of organic layers.

In another exemplary embodiment, the organic light emitting device may be an organic light emitting device having a structure (normal type) where an anode, organic material layers of one or more layers, and a cathode are sequentially laminated on a substrate.

In another exemplary embodiment, the organic light emitting device may be an organic light emitting device having an inverted direction structure (inverted type) where the cathode, the organic material layers of one or more layers, and the anode are sequentially laminated on the substrate.

In the exemplary embodiment of the present specification, the first electrode is the cathode, and the second electrode is the anode. In another exemplary embodiment, the first electrode is the anode, and the second electrode is the cathode.

Figure 2:
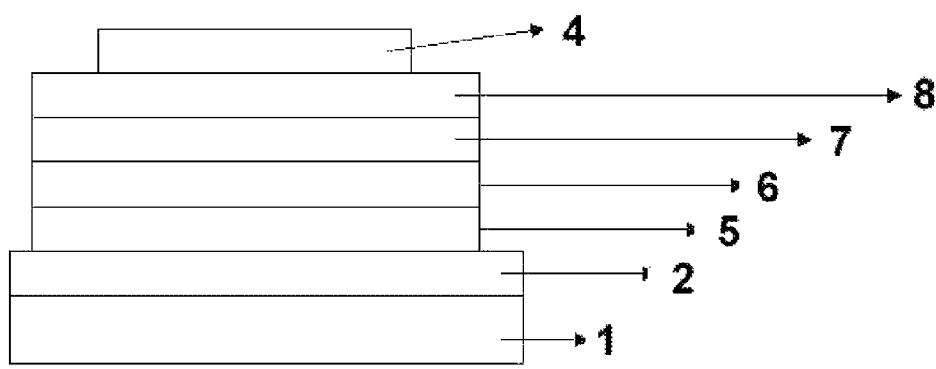
FIG. 2 illustrates an example of an organic light emitting device including a substrate 1, an anode 2, a hole injection layer 5, a hole transport layer 6, a light emitting layer 7, an electron transport layer 8, and a cathode 4.

The structure of the organic light emitting device of the present specification is illustrated in FIGS. 1 and 2, but is not limited thereto.

FIG. 1 illustrates a structure of an organic light emitting device where a substrate 1, an anode 2, a light emitting layer 3, and a cathode 4 are sequentially laminated. In the aforementioned structure, the compound may be included in the light emitting layer 3.

FIG. 2 illustrates a structure of an organic light emitting device where the substrate 1, the anode 2, a hole injection layer 5, a hole transport layer 6, a light emitting layer 7, an electron transport layer 8, and the cathode 4 are sequentially laminated. In the aforementioned structure, the compound may be included in one or more layers of the hole injection layer 5, the hole transport layer 6, the light emitting layer 7, and the electron transport layer 8.

The organic light emitting device of the present specification may be manufactured by a material and a method known in the art, except that one or more layers of organic material layers include the compound of the present specification, that is, the heterocyclic compound or the compound in which the heat-curable or photo-curable functional group is introduced into the heterocyclic compound.

For example, the organic light emitting device of the present specification may be manufactured by sequentially laminating the first electrode, the organic material layer, and the second electrode on the substrate. In this case, the organic light emitting device may be manufactured by depositing metal, metal oxides having conductivity, or an alloy thereof on the substrate by using a PVD (physical vapor deposition) method such as a sputtering method or an e-beam evaporation method to form the anode, forming the organic material layer including the hole injection layer, the hole transport layer, the light emitting layer, and the electron transport layer thereon, and then depositing a material that can be used as the cathode thereon. In addition to this method, the organic light emitting device may be manufactured by sequentially depositing a cathode material, the organic material layer, and an anode material on the substrate.

Further, the heterocyclic compound may be formed into the organic material layer by a solution coating method as well as a vacuum deposition method when the organic light emitting device is manufactured. Herein, the solution coating method means spin coating, dip coating, doctor blading, inkjet printing, screen printing, a spray method, roll coating, or the like, but is not limited thereto.

The substrate may be selected in consideration of optical and physical properties, if necessary. For example, it is preferable that the substrate be transparent. A hard material may be used in the substrate, but the substrate may be formed of a flexible material such as plastic.

Examples of the material of the substrate may include, in addition to glass and quartz, PET (polyethylene terephthalate), PEN (polyethylene naphthalate), PP (polypropylene), PI (polyimide), PC (polycarbonate), PS (polystyrene), POM (polyoxymethylene), an AS resin (acrylonitrile styrene copolymer), an ABS resin (acrylonitrile butadiene styrene copolymer), TAC (triacetyl cellulose), PAR (polyarylate), and the like, but are not limited thereto.

It is preferable that the cathode material be, in general, a material having a small work function so as to easily inject electrons into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

It is preferable that the anode material be, in general, a material having a large work function so as to smoothly inject holes into the organic material layer. Specific examples of the anode material that can be used in the present specification include metals such as vanadium, chrome, copper, zinc, and gold, or an alloy thereof; metal oxides such as zinc oxides, indium oxides, indium tin oxides (ITO), and indium zinc oxides (IZO); a combination of metal and oxide, such as ZnO:Al or $SnO_2$:Sb; conductive polymers such as poly(3-methylthiophene), poly[3,4-(ethylene-1,2-dioxy)thiophene] (PEDOT), polypyrrole, and polyaniline, and the like, but are not limited thereto.

The hole transport layer is a layer receiving the holes from the hole injection layer and transporting the holes to the light emitting layer, the hole transport material is a material capable of receiving the holes from the anode or the hole injection layer and transporting the holes to the light emitting layer, and a material having large mobility of the holes is suitable. Specific examples thereof include an arylamine-based organic material, a conductive polymer, a block copolymer in which a conjugate portion and a non-conjugate portion are present together, and the like, but are not limited thereto.

The hole injection layer is a layer injecting the holes from the electrode, and it is preferable that the hole injection material be a compound which has an ability of transporting the holes to have a hole injection effect in the anode and an excellent hole injection effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material be between the work function of the anode material and a HOMO of a peripheral organic material layer. Specific examples of the hole injection material include metal porphyrin, oligothiophene, an arylamine-based organic material, a phthalocyanine derivative, a hexanitrilehexaazatriphenylene-based organic material, a quinacridone-based organic material, a perylene-based organic material, anthraquinone, and polyaniline and polythiophene-based conductive polymers, and the like, but are not limited thereto.

The light emitting material is a material that can receive the holes and the electrons from the hole transport layer and the electron transport layer, respectively, and bond the holes and the electrons to emit light in a visible ray region, and is preferably a material having good quantum efficiency to fluorescence or phosphorescence. Specific examples thereof include a 8-hydroxy-quinoline aluminum complex ($Alq_3$); a carbazole-based compound; a dimerized styryl compound; BAlq; a 10-hydroxybenzoquinoline-metal compound; benzoxazole, benzthiazole, and benzimidazole-based compounds; a poly(p-phenylenevinylene) (PPV)-based polymer; a spiro compound; polyfluorene, lubrene, and the like, but are not limited thereto.

The light emitting layer may include a host material and a dopant material. Examples of the host material include a condensation aromatic cycle derivative, a heterocycle-containing compound, or the like. Specific examples of the compensation aromatic cycle derivative include an anthracene derivative, a pyrene derivative, a naphthalene derivative, a pentacene derivative, a phenanthrene compound, a fluoranthene compound, and the like, and specific examples of the heterocycle-containing compound include a carbazole derivative, a dibenzofuran derivative, a ladder-type furan compound, a pyrimidine derivative, and the like, but the examples are not limited thereto.

Examples of the dopant material include an aromatic amine derivative, a styrylamine compound, a boron complex, a fluoranthene compound, a metal complex, and the like. Specifically, the aromatic amine derivative is a compensation aromatic cycle derivative having a substituted or unsubstituted arylamino group, examples thereof include pyrene, anthracene, chrysene, and periflanthene having the arylamino group, and the like, the styrylamine compound is a compound where at least one arylvinyl group is substituted in substituted or unsubstituted arylamine, and in the styrylamine compound, one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron injection layer is a layer injecting the electrons from the electrode, and a compound which has an ability of transporting the electrons, an electron injection effect from the cathode, and an excellent electron injection effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and derivatives thereof, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris (2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2- methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility of the electrons is suitable. Specific examples thereof include an 8-hydroxyquinoline Al complex; a complex including $Alq_3$; an organic radical compound; a hydroxyflavone-metal complex, and the like, but are not limited thereto.

The hole blocking layer is a layer blocking arrival of the holes at the cathode, and in general, may be formed under the same condition as the hole injection layer. Specific examples thereof include an oxadiazole derivative, a triazole derivative, a phenanthroline derivative, BCP, an aluminum complex, and the like, but are not limited thereto.

In the exemplary embodiment of the present specification, the organic light emitting device may be a top emission type, a bottom emission type, or a both-sided emission type according to the used material.

A method of synthesizing the organic compound represented by Chemical Formula 1 or Chemical Formula 2 and manufacturing of the organic light emitting device using the same will be described in more detail by the following Examples and Comparative Examples. However, the Examples are set to illustrate the present specification but are not to be construed to limit the scope of the present specification.

PREPARATION EXAMPLE 1

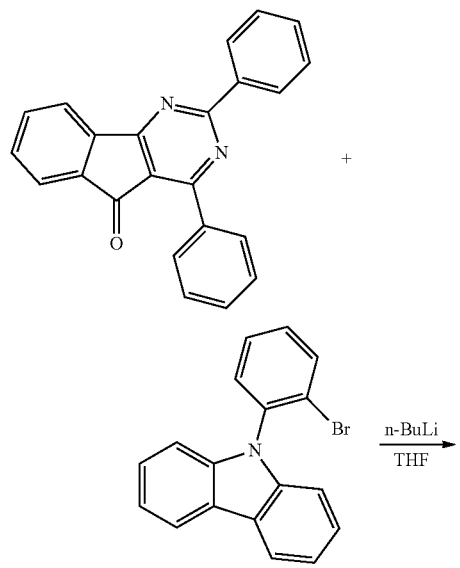

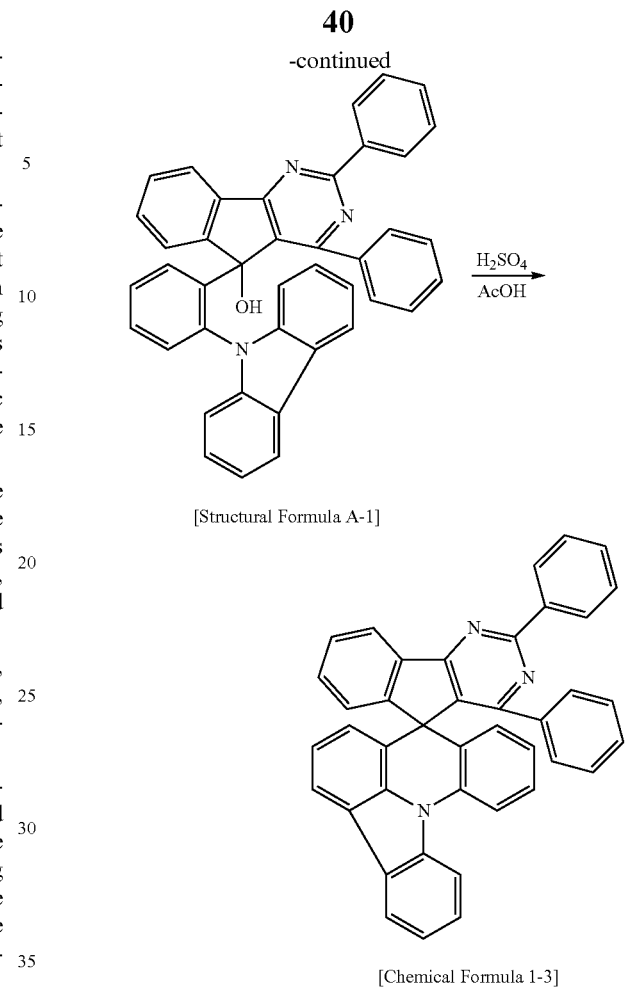

1) Preparation of Structural Formula A-1

9-(2-bromophenyl)-carbazole (20.9 g, 62.1 mmol) was dissolved in anhydrous tetrahydrofuran (THF) (200 ml) and then cooled to −78° C. 2.5M n-butyllithium (n-Bu-Li) (24.8 ml, 62.1 mmol) was added for 30 minutes and then agitated at −78° C. for 2 hours. After 2,4-diphenyl-indeno[1,2-d]pyrimidine-5-one (18.9 g, 56.4 mmol) was added at −78° C., the temperature was increased to normal temperature, and the reaction was quenched by the ammonium chloride aqueous solution (aq. $NH_4Cl$). After the organic layer was separated, concentration was performed and purification was performed by the chromatography to obtain Structural Formula A-1 (15 g, 26 mmol).

Figure 3:
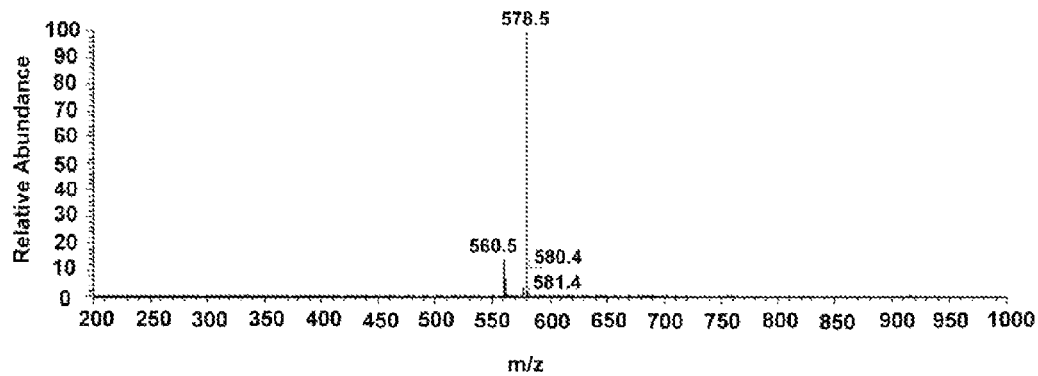
FIG. 3 is a view illustrating an MS spectrum of Structural Formula A-1 prepared in Preparation Example 1.

FIG. 3 is a view illustrating an MS spectrum of Structural Formula A-1.

2) Preparation of Chemical Formula 1-3

After Structural Formula A-1 (15 g, 26 mmol) obtained in the aforementioned reaction was dissolved in the acetic acid (200 ml), 1 g of the concentrated sulfuric acid ($H_2SO_4$) was added. After reflux for 24 hours, cooling to normal temperature was performed. Water ($H_2O$) (500 ml) was added to generate the solid. After filtration, the solid was purified by the chromatography to obtain Chemical Formula 1-3 (6.5 g, yield 45%).

MS: $[M+H]^+=560$

Figure 4:
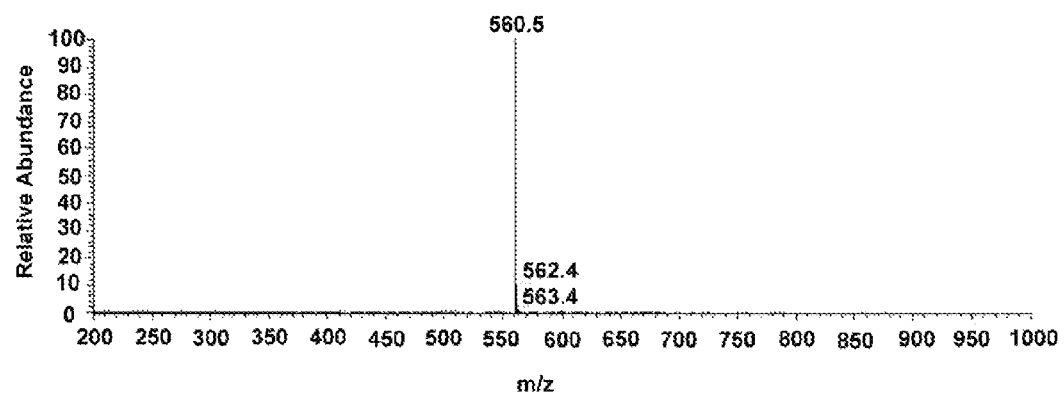
FIG. 4 is a view illustrating an MS spectrum of Chemical Formula 1-3 prepared in Preparation Example 1.

FIG. 4 is a view illustrating an MS spectrum of a compound of Chemical Formula 1-3.

PREPARATION EXAMPLE 2

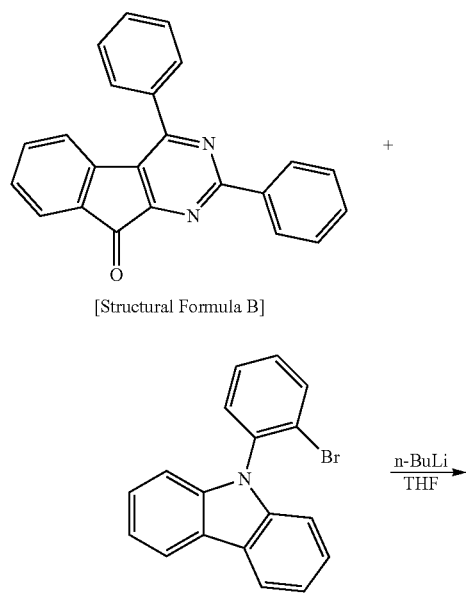

[Structural Formula B]

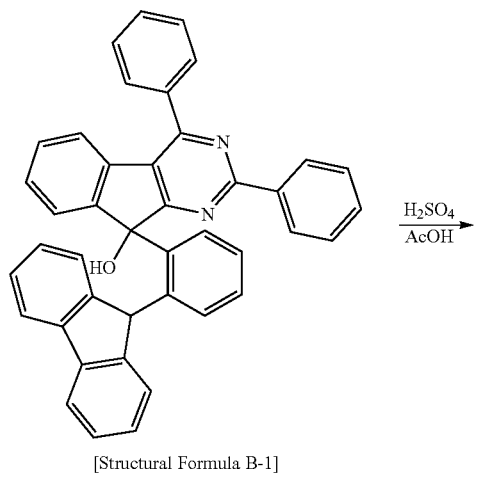

[Structural Formula B-1]

[Chemical Formula 1-4]

1) Preparation of Structural Formula B-1

9-(2-bromophenyl)-carbazole (20.9 g, 62.1 mmol) was dissolved in anhydrous tetrahydrofuran (THF) (200 ml) and then cooled to −78° C. 2.5M n-butyllithium (n-Bu-Li) (24.8 ml, 62.1 mmol) was added for 30 minutes and then agitated at −78° C. for 2 hours. After Structural Formula B (18.9 g, 56.4 mmol) was added at −78° C., the temperature was increased to normal temperature, and the reaction was quenched by the ammonium chloride aqueous solution (aq. NH$_4$Cl). After the organic layer was separated, concentration was performed and purification was performed by the chromatography to obtain Structural Formula B-1 (17.3 g, yield 52%).

2) Preparation of Chemical Formula 1-4

After Structural Formula B-1 (17.3 g, 29.9 mmol) obtained in the aforementioned reaction was dissolved in acetic acid (200 ml), 1 g of the concentrated sulfuric acid (H$_2$SO$_4$) was added. After reflux for 24 hours, cooling to normal temperature was performed. Water (H$_2$O) (500 ml) was added to generate a solid. After filtration, the solid was purified by the chromatography to obtain Chemical Formula 1-4 (5.5 g, yield 33%).

MS: [M+H]$^+$=560

PREPARATION EXAMPLE 3

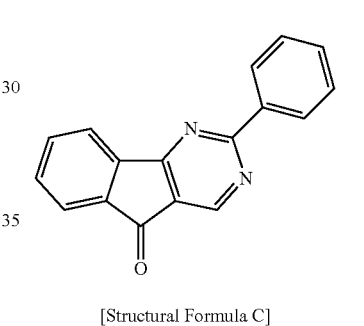

[Structural Formula C]

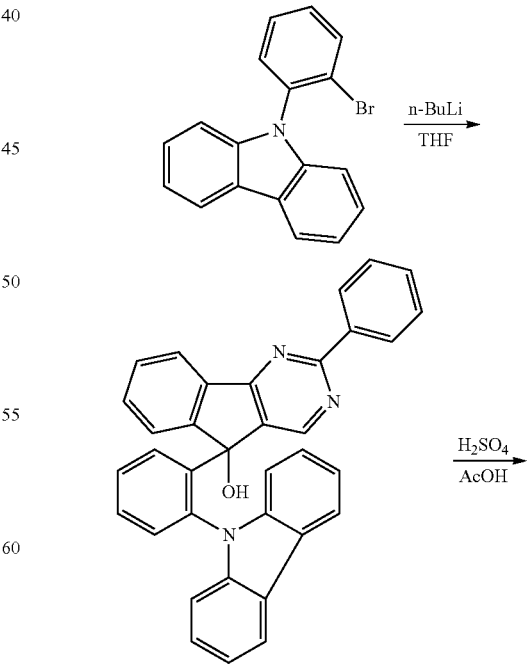

[Structural Formula C-1]

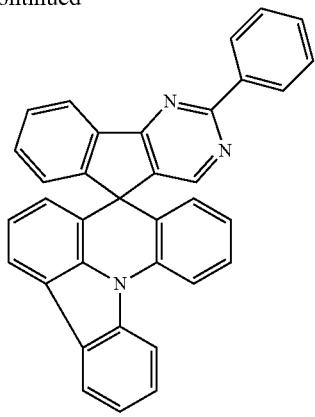

[Chemical Formula 1-1]

1) Preparation of Structural Formula C-1

9-(2-bromophenyl)-carbazole (10 g, 31.0 mmol) was dissolved in anhydrous tetrahydrofuran (THF) (200 ml) and then cooled to −78° C. 2.5M n-butyllithium (n-Bu-Li) (12.4 ml, 31.0 mmol) was added for 30 minutes and then agitated at −78° C. for 2 hours. After Structural Formula C (7.3 g, 28.2 mmol) was added at −78° C., the temperature was increased to normal temperature, and the reaction was quenched by the ammonium chloride aqueous solution (aq. $NH_4Cl$). After the organic layer was separated, concentration was performed and purification was performed by the chromatography to obtain Structural Formula C-1 (5.8 g, yield 41%).

2) Preparation of Chemical Formula 1-1

After Structural Formula C-1 (5.8 g, 11.6 mmol) obtained in the aforementioned reaction was dissolved in the acetic acid (100 ml), 1 g of the concentrated sulfuric acid ($H_2SO_4$) was added. After reflux for 24 hours, cooling to normal temperature was performed. Water ($H_2O$) (500 ml) was added to generate the solid. After filtration, the solid was purified by the chromatography to obtain Chemical Formula 1-1 (2.9 g, yield 52%).

MS: $[M+H]^+=483$

PREPARATION EXAMPLE 4

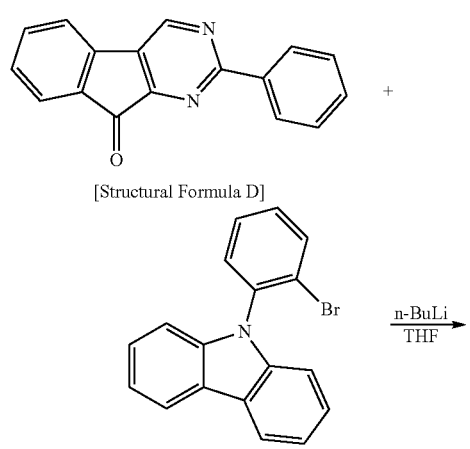

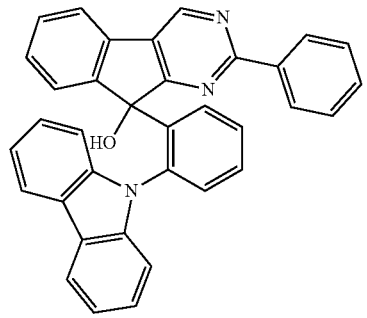

[Structural Formula D-1]

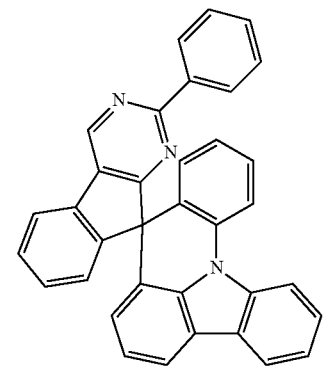

[Chemical Formula 1-2]

1) Preparation of Structural Formula D-1

9-(2-bromophenyl)-carbazole (10 g, 31.0 mmol) was dissolved in anhydrous tetrahydrofuran (THF) (200 ml) and then cooled to −78° C. 2.5M n-butyllithium (n-Bu-Li) (12.4 ml, 31.0 mmol) was added for 30 minutes and then agitated at −78° C. for 2 hours. After Structural Formula D (7.3 g, 28.2 mmol) was added at −78° C., the temperature was increased to normal temperature, and the reaction was quenched by the ammonium chloride aqueous solution (aq. $NH_4Cl$). After the organic layer was separated, concentration was performed and purification was performed by the chromatography to obtain Structural Formula D-1 (6.1 g, yield 43%).

2) Preparation of Chemical Formula 1-2

After Structural Formula D-1 (5.8 g, 12.2 mmol) obtained in the aforementioned reaction was dissolved in the acetic acid (100 ml), 1 g of the concentrated sulfuric acid ($H_2SO_4$) was added. After reflux for 24 hours, cooling to normal temperature was performed. Water ($H_2O$) (500 ml) was added to generate the solid. After filtration, the solid was purified by the chromatography to obtain Chemical Formula 1-2 (2.5 g, yield 45%).

MS: $[M+H]^+=483$

PREPARATION EXAMPLE 5

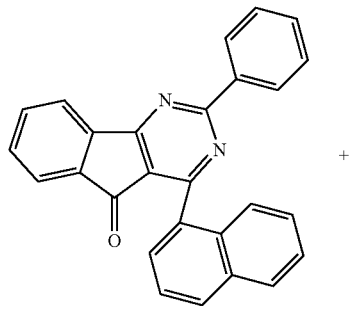

[Structural Formula E]

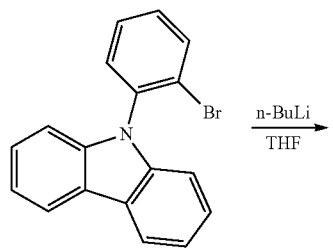

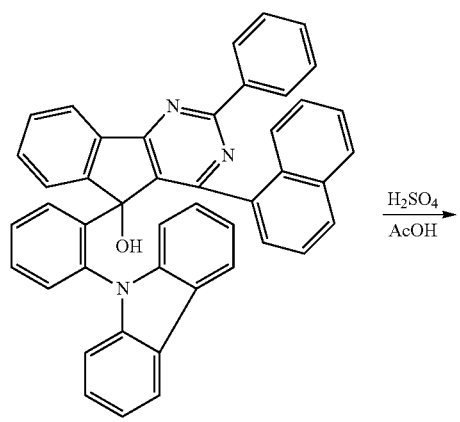

[Structural Formula E-1]

[Structural Formula 1-13]

1) Preparation of Structural Formula E-1

9-(2-bromophenyl)-carbazole (15 g, 46.5 mmol) was dissolved in anhydrous tetrahydrofuran (THF) (200 ml) and then cooled to −78° C. 2.5M n-butyllithium (n-Bu-Li) (18.6 ml, 46.5 mmol) was added for 30 minutes and then agitated at −78° C. for 2 hours. After Structural Formula E (14.9 g, 38.8 mmol) was added at −78° C., the temperature was increased to normal temperature, and the reaction was quenched by the ammonium chloride aqueous solution (aq. $NH_4Cl$). After the organic layer was separated, concentration was performed and purification was performed by the chromatography to obtain Structural Formula E-1 (11.7 g, yield 48%).

2) Preparation of Chemical Formula 1-13

After Structural Formula E-1 (11.7 g, 18.6 mmol) obtained in the aforementioned reaction was dissolved in the acetic acid (100 ml), 1 g of the concentrated sulfuric acid ($H_2SO_4$) was added. After reflux for 24 hours, cooling to normal temperature was performed. Water ($H_2O$) (500 ml) was added to generate the solid. After filtration, the solid was purified by the chromatography to obtain Chemical Formula 1-13 (4.1 g, yield 36%).

MS: $[M+H]^+$=609

PREPARATION EXAMPLE 6

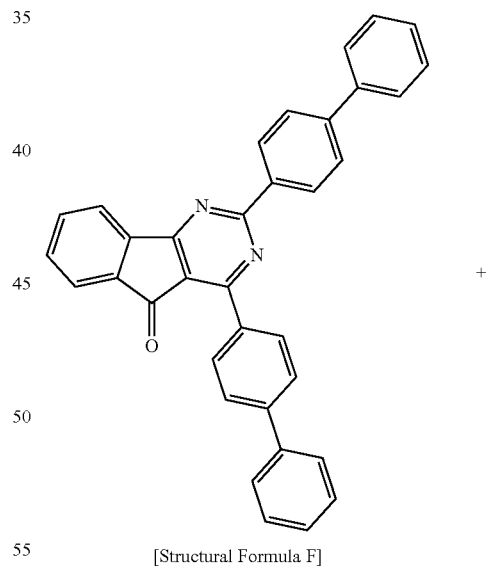

[Structural Formula F]

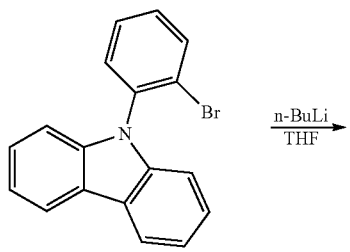

PREPARATION EXAMPLE 7

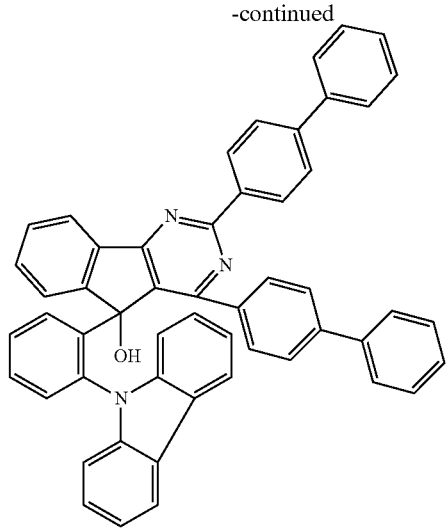

[Structural Formula F-1]

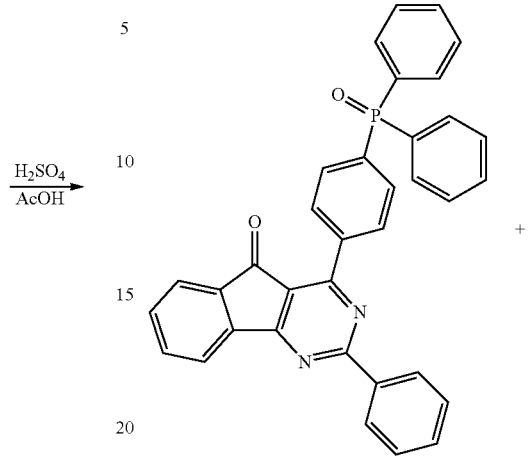

[Structural Formula G]

+

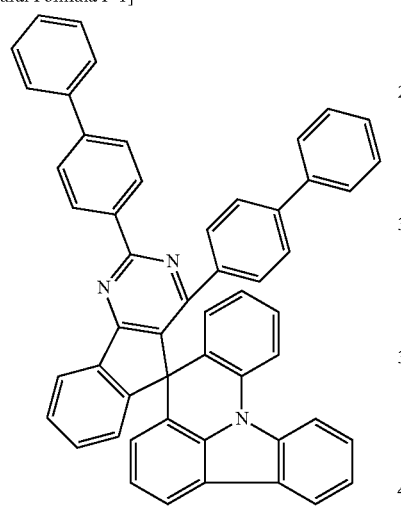

[Chemical Formula 1-11]

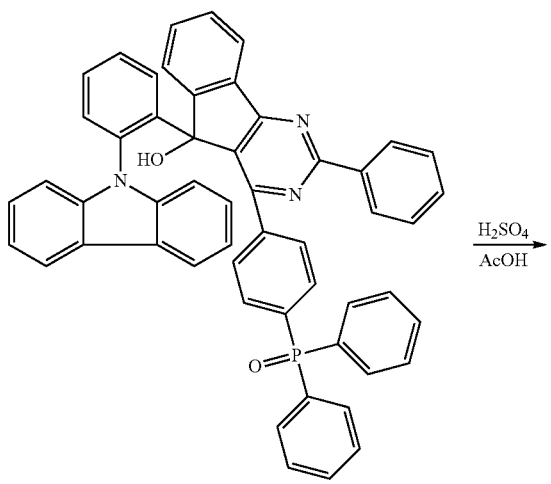

[Structural Formula G-1]

1) Preparation of Structural Formula F-1

9-(2-bromophenyl)-carbazole (10 g, 31.0 mmol) was dissolved in anhydrous tetrahydrofuran (THF) (200 ml) and then cooled to −78° C. 2.5M n-butyllithium (n-Bu-Li) (12.4 ml, 31.0 mmol) was added for 30 minutes and then agitated at −78° C. for 2 hours. After Structural Formula F (12.5 g, 25.8 mmol) was added at −78° C., the temperature was increased to normal temperature, and the reaction was quenched by the ammonium chloride aqueous solution (aq. $NH_4Cl$). After the organic layer was separated, concentration was performed and purification was performed by the chromatography to obtain Structural Formula F-1 (11.1 g, yield 59%).

2) Preparation of Chemical Formula 1-11

After Structural Formula F-1 (11.1 g, 15.2 mmol) obtained in the aforementioned reaction was dissolved in the acetic acid (100 ml), 1 g of the concentrated sulfuric acid ($H_2SO_4$) was added. After reflux for 24 hours, cooling to normal temperature was performed. Water ($H_2O$) (500 ml) was added to generate the solid. After filtration, the solid was purified by the chromatography to obtain Chemical Formula 1-11 (5.7 g, yield 53%).

MS: $[M+H]^+$=711

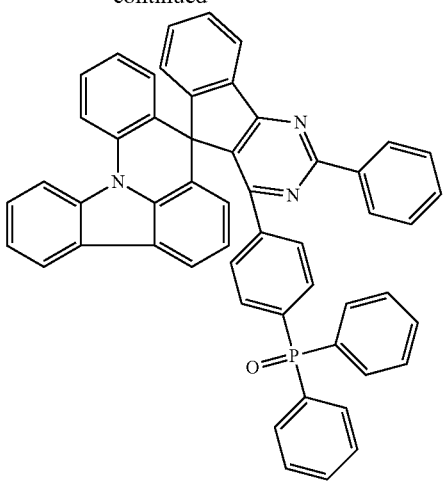

[Structural Formula 1-19]

1) Preparation of Structural Formula G-1

9-(2-bromophenyl)-carbazole (10 g, 31.0 mmol) was dissolved in anhydrous tetrahydrofuran (THF) (200 ml) and then cooled to −78° C. 2.5M n-butyllithium (n-Bu-Li) (12.4 ml, 31.0 mmol) was added for 30 minutes and then agitated at −78° C. for 2 hours. After Structural Formula G (13.8 g, 25.8 mmol) was added at −78° C., the temperature was increased to normal temperature, and the reaction was quenched by the ammonium chloride aqueous solution (aq. NH$_4$Cl). After the organic layer was separated, concentration was performed and purification was performed by the chromatography to obtain Structural Formula G-1 (5.2 g, yield 26%).

2) Preparation of Chemical Formula 1-19

After Structural Formula G-1 (5.2 g, 6.7 mmol) obtained in the aforementioned reaction was dissolved in acetic acid (50 ml), 0.1 g of concentrated sulfuric acid (H$_2$SO$_4$) was added. After reflux for 24 hours, cooling to normal temperature was performed. Water (H$_2$O) (200 ml) was added to generate the solid. After filtration, the solid was recrystallized by using ethyl acetate and hexane to obtain Chemical Formula 1-19 (2.8 g, yield 56%).

MS: [M+H]$^+$=759

PREPARATION EXAMPLE 8

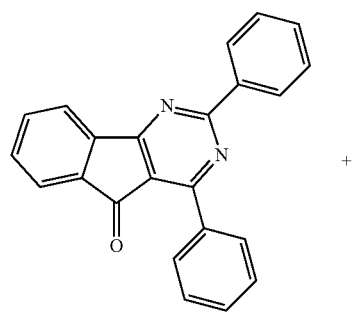

[Structural Formula H]

+

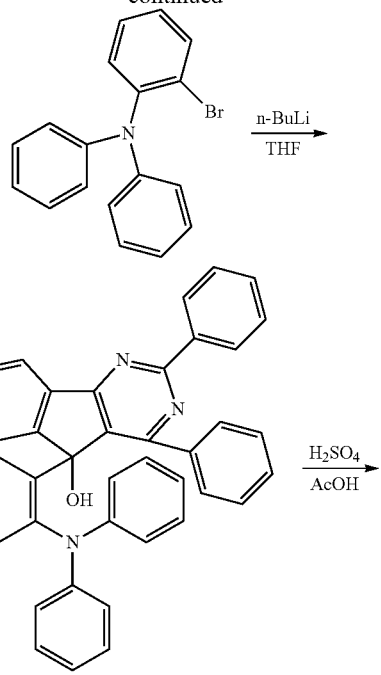

[Structural Formula H-1]

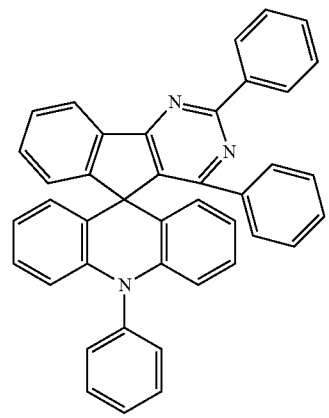

[Structural Formula 2-3]

1) Preparation of Structural Formula H-1

Structural Formula H (15 g, 46.3 mmol) was dissolved in anhydrous tetrahydrofuran (THF) (200 ml) and then cooled to −78° C. 2.5M n-butyllithium (n-Bu-Li) (18.5 ml, 46.3 mmol) was added for 30 minutes and then agitated at −78° C. for 2 hours. After 2,4-diphenyl-indeno[1,2-d]pyrimidine-5-one (12.9 g, 38.6 mmol) was added at −78° C., the temperature was increased to normal temperature, and the reaction was quenched by the ammonium chloride aqueous solution (aq. NH$_4$Cl). After the organic layer was separated, concentration was performed and purification was performed by the chromatography to obtain Structural Formula H-1 (14.1 g, yield 63%).

2) Preparation of Chemical Formula 2-3

After Structural Formula H-1 (14.1 g, 24.3 mmol) obtained in the aforementioned reaction was dissolved in acetic acid (150 ml), 1 g of concentrated sulfuric acid (H$_2$SO$_4$) was added. After reflux for 24 hours, cooling to normal temperature was performed. Water (H$_2$O) (500 ml) was added to generate the solid. After filtration, the solid was purified by the chromatography to obtain Chemical Formula 2-3 (6.4 g, yield 47%).

MS: [M+H]$^+$=561

EXAMPLE 1

Light Emitting Layer

A glass substrate on which a thin film of ITO (indium tin oxide) was applied in a thickness of 500 Å was put into distilled water having the detergent dissolved therein and washed by the ultrasonic wave. In this case, the product manufactured by Fischer Co., was used as the detergent, and distilled water, which had been twice filtered by the filter manufactured by Millipore Co., was used as the distilled water. The ITO was washed for 30 minutes, and washing with ultrasonic waves was then repeated twice for 10 minutes using distilled water. After the washing with distilled water was finished, washing with ultrasonic waves was performed by solvents such as isopropyl alcohol, acetone, and methanol, and the ITO was dried and transported to the plasma washing machine. Further, the substrate was washed by using oxygen plasma for 5 minutes, and then transported to the vacuum deposition machine.

Hexanitrile hexaazatriphenylene (HAT) of the following Chemical Formula was thermally deposited under vacuum in a thicknesses of 500 Å on the ITO transparent electrode thus prepared to form a hole injection layer.

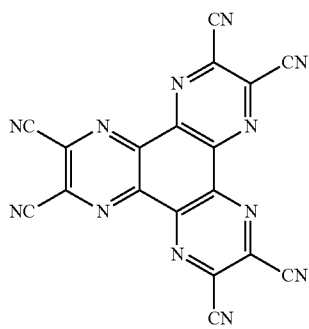

[HAT]

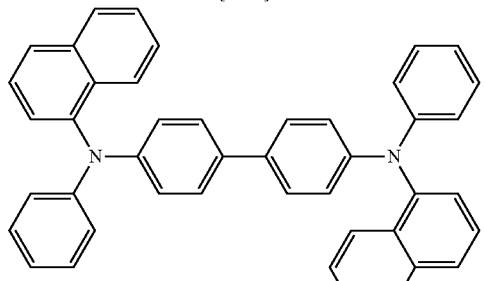

[NPB]

4,4'-bis[N-(1-naphthyl)-N-phenylamino]biphenyl (NPB) (250 Å), hexanitrile hexaazatriphenylene (HAT) (50 Å), and 4,4'-bis[N-(1-naphthyl)-N-phenylamino]biphenyl (NPB) (400 Å) of the aforementioned Chemical Formulas were sequentially deposited under vacuum on the hole injection layer to form a hole transport layer.

Subsequently, the manufactured compound of Chemical Formula 1-3 and a dopant compound GD as illustrated below were deposited under vacuum at a weight ratio of 10:1 in a film thickness of 300 Å on the hole transport layer to form a light emitting layer.

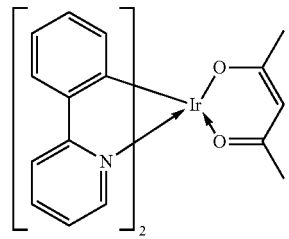

[GD]

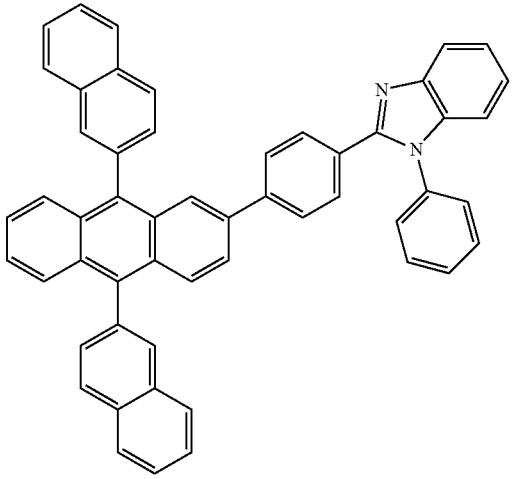

[ET-A]

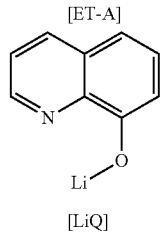

[LiQ]

The compound of Chemical Formula ET-A and the aforementioned Chemical Formula LiQ (lithium quinalate) were deposited under vacuum as the electron transport layer material at a weight ratio of 1:1 on the light emitting layer to form an electronic injection and transport layer in a thickness of 300 Å.

Lithium fluoride (LiF) in a thickness of 15 Å and aluminum in a thickness of 1,000 Å were subsequently deposited on the electron injection and transport layer to form a cathode.

In the aforementioned process, the deposition speed of the organic material was maintained at 0.4 to 0.7 Å/sec, the deposition speed of lithium fluoride of the cathode was maintained at 0.3 Å/sec, the deposition speed of aluminum was maintained at 2 Å/sec, and the degree of vacuum during deposition was maintained at $2\times10^{-7}$ to $5\times10^{-8}$ torr to manufacture an organic light emitting device.

EXAMPLE 2

Light Emitting Layer

An organic light emitting device was manufactured by the same method as Example 1, except that the prepared compound of Chemical Formula 1-4 was used instead of the compound of Chemical Formula 1-3 of Example 1.

EXAMPLE 3

Light Emitting Layer

An organic light emitting device was manufactured by the same method as Example 1, except that the prepared compound of Chemical Formula 1-1 was used instead of the compound of Chemical Formula 1-3 of Example 1.

EXAMPLE 4

Light Emitting Layer

An organic light emitting device was manufactured by the same method as Example 1, except that the prepared compound of Chemical Formula 1-2 was used instead of the compound of Chemical Formula 1-3 of Example 1.

EXAMPLE 5

Light Emitting Layer

An organic light emitting device was manufactured by the same method as Example 1, except that the prepared compound of Chemical Formula 1-13 was used instead of the compound of Chemical Formula 1-3 of Example 1.

EXAMPLE 6

Light Emitting Layer

An organic light emitting device was manufactured by the same method as Example 1, except that the prepared compound of Chemical Formula 1-11 was used instead of the compound of Chemical Formula 1-3 of Example 1.

EXAMPLE 7

Light Emitting Layer

An organic light emitting device was manufactured by the same method as Example 1, except that the prepared compound of Chemical Formula 1-19 was used instead of the compound of Chemical Formula 1-3 of Example 1.

EXAMPLE 8

Light Emitting Layer

An organic light emitting device was manufactured by the same method as Example 1, except that the prepared compound of Chemical Formula 2-3 was used instead of the compound of Chemical Formula 1-3 of Example 1.

COMPARATIVE EXAMPLE 1

An organic light emitting device was manufactured by the same method as Example 1, except that the compound of the following Chemical Formula GH-A was used instead of the compound of Chemical Formula 1-9 of Example 1.

[GH-A]

When the current (10 mA/cm$^2$) was applied to the organic light emitting devices manufactured in the Examples and Comparative Example 1, the results of the following Table 1 were obtained.

TABLE 1

|  | Compound | Voltage (V) | Efficiency (cd/A) |
|---|---|---|---|
| Example 1 | Chemical Formula 1-3 | 4.65 | 67.5 |
| Example 2 | Chemical Formula 1-4 | 4.80 | 69.2 |
| Example 3 | Chemical Formula 1-1 | 4.93 | 58.6 |
| Example 4 | Chemical Formula 1-2 | 4.95 | 57.7 |
| Example 5 | Chemical Formula 1-13 | 4.21 | 40.6 |
| Example 6 | Chemical Formula 1-11 | 4.60 | 67.7 |
| Example 7 | Chemical Formula 1-19 | 4.10 | 58.3 |
| Example 8 | Chemical Formula 2-3 | 4.10 | 65.2 |
| Comparative Example 1 | GH-A | 6.12 | 15.26 |

From the results of Table 1, it can be seen that the new compound according to the present invention may be used as a material of a light emitting layer of an organic electronic device including an organic light emitting device, and the organic electronic device including the organic light emitting device using the same exhibits excellent properties in views of efficiency, driving voltage, stability and the like. Particularly, the compound may reduce the driving voltage and induce an increase in efficiency to improve power consumption.

What is claimed is:

1. A heterocyclic compound represented by the following Chemical Formula 1 or 2:

[Chemical Formula 1]

[Chemical Formula 2]

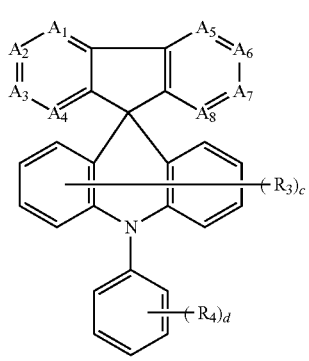

wherein a is an integer of 7,
b is an integer of 4,
c is an integer of 8,
d is an integer of 5,
$A_1$ to $A_4$ are CR,
$A_5$ and $A_7$ are N, $A_6$ and $A_8$ are CR; or $A_6$ and $A_8$ are N, and $A_5$ and $A_7$ are CR and
R and $R_1$ to $R_4$ are the same as or different from each other, and are each independently hydrogen; deuterium; a halogen group; a nitrile group; a nitro group; a hydroxy group; a carbonyl group; an ester group; an imide group; an amide group; a substituted or unsubstituted alkyl group; a substituted or unsubstituted cycloalkyl group; a substituted or unsubstituted alkoxy group; a substituted or unsubstituted aryloxy group; a substituted or unsubstituted alkylthioxy group; a substituted or unsubstituted arylthioxy group; a substituted or unsubstituted alkylsulfoxy group; a substituted or unsubstituted arylsulfoxy group; a substituted or unsubstituted alkenyl group; a substituted or unsubstituted silyl group; a substituted or unsubstituted boron group; a substituted or unsubstituted alkylamine group; a substituted or unsubstituted aralkylamine group; a substituted or unsubstituted arylamine group; a substituted or unsubstituted heteroarylamine group; a substituted or unsubstituted arylphosphine group; a substituted or unsubstituted phosphine oxide group; a substituted or unsubstituted aryl group; or a substituted or unsubstituted heterocyclic group including one or more of N, O, and S atoms.

2. The heterocyclic compound of claim 1, wherein R is hydrogen; a substituted or unsubstituted aryl group; or a substituted or unsubstituted heterocyclic group including one or more of N, O, and S atoms.

3. The heterocyclic compound of claim 1, wherein R is hydrogen; an aryl group unsubstituted or substituted with one or two or more substituent groups selected from the group consisting of the substituted or unsubstituted phosphine oxide group, the substituted or unsubstituted aryl group, and the substituted or unsubstituted heterocyclic group including one or more of the N, O, and S atoms; or a heterocyclic group including one or more of N, O, and S atoms unsubstituted or substituted with one or two or more substituent groups selected from the group consisting of the substituted or unsubstituted phosphine oxide group, the substituted or unsubstituted aryl group, and the substituted or unsubstituted heterocyclic group including one or more of the N, O, and S atoms.

4. The heterocyclic compound of claim 1, wherein the heterocyclic compound represented by Chemical Formula 1 is is represented by any one of the following Chemical Formulas 1-1 to 1-36:

Chemical Formula 1-1

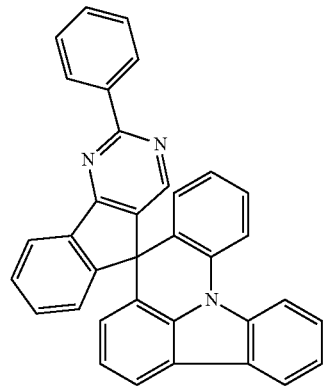

Chemical Formula 1-2

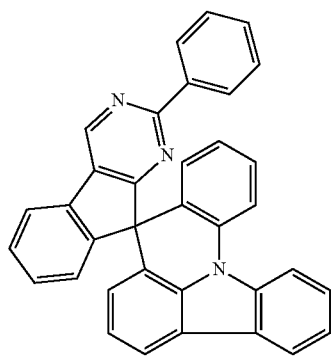

Chemical Formula 1-3

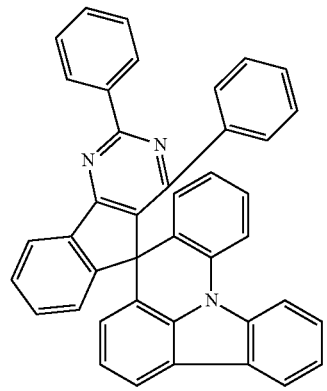

Chemical Formula 1-4

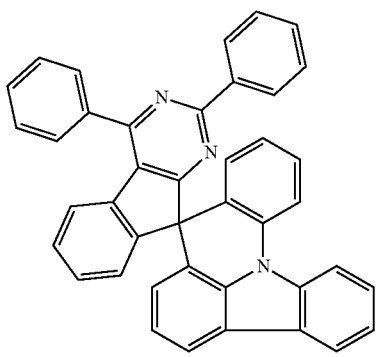

Chemical Formula 1-5
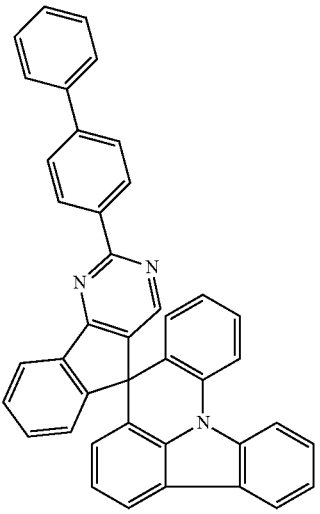
Chemical Formula 1-6
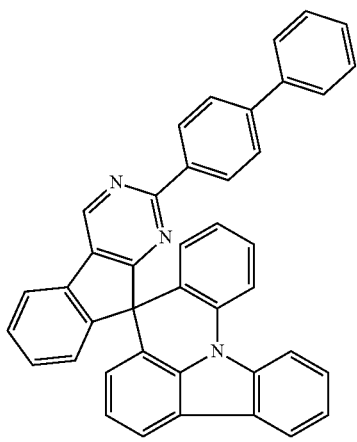
Chemical Formula 1-7
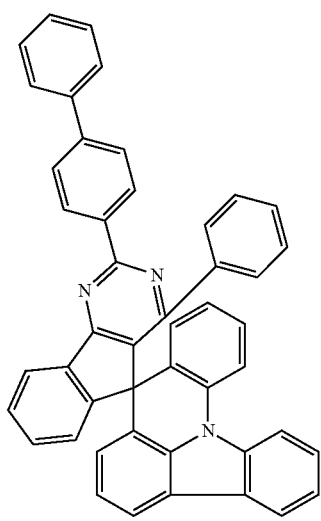
Chemical Formula 1-8
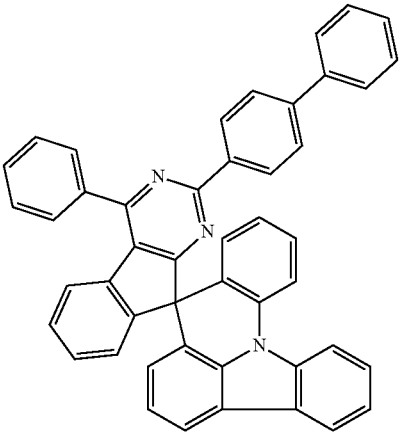
Chemical Formula 1-9
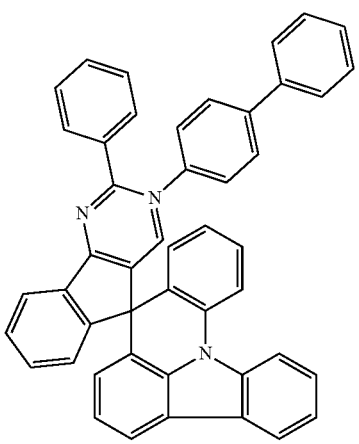
Chemical Formula 1-10
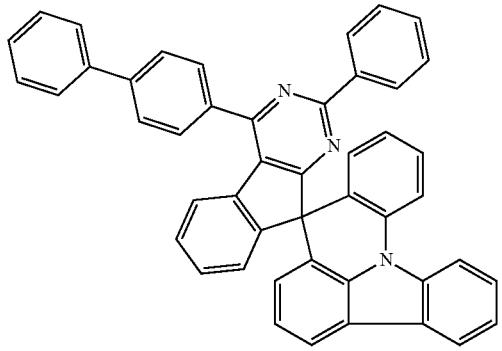

Chemical Formula 1-11
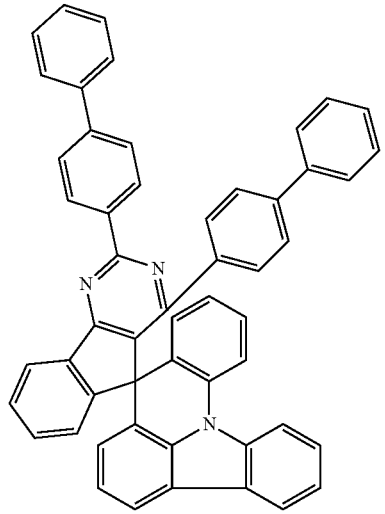
Chemical Formula 1-12
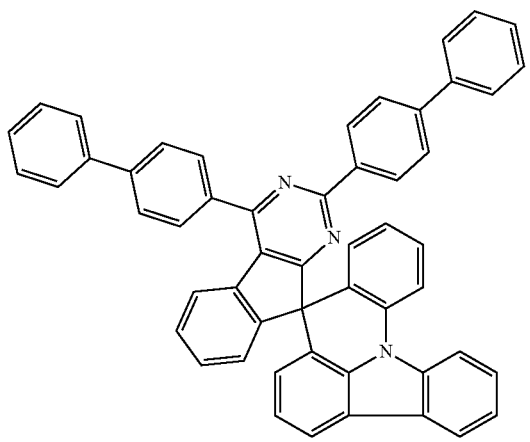
Chemical Formula 1-13
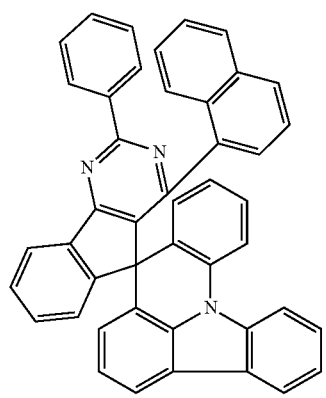
Chemical Formula 1-14
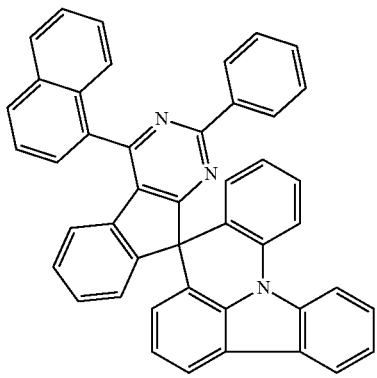
Chemical Formula 1-15
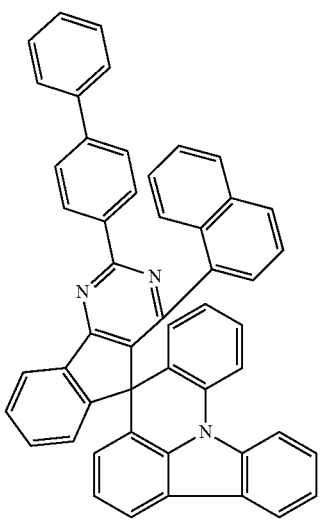
Chemical Formula 1-16
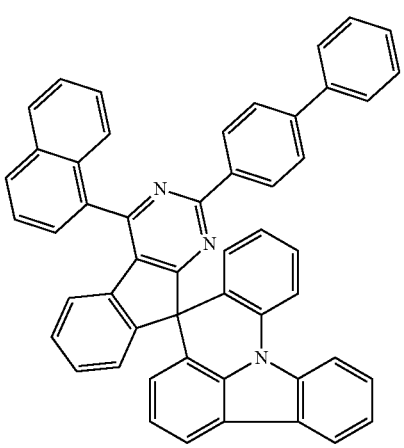

Chemical Formula 1-17
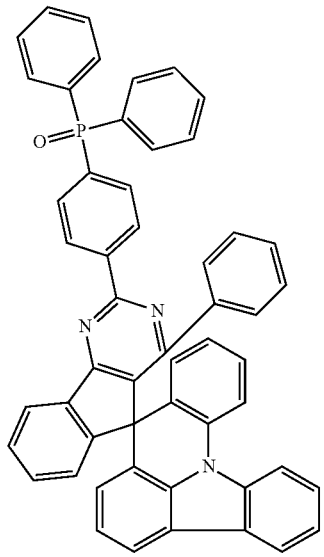
Chemical Formula 1-18
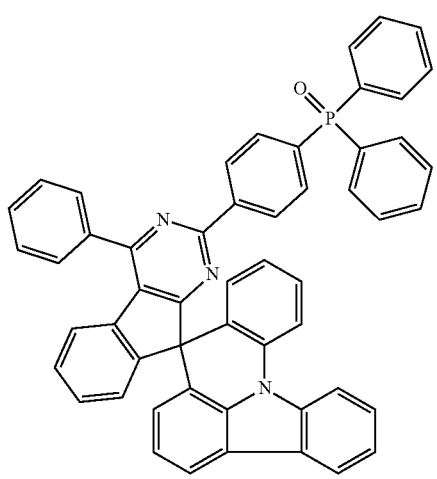
Chemical Formula 1-19
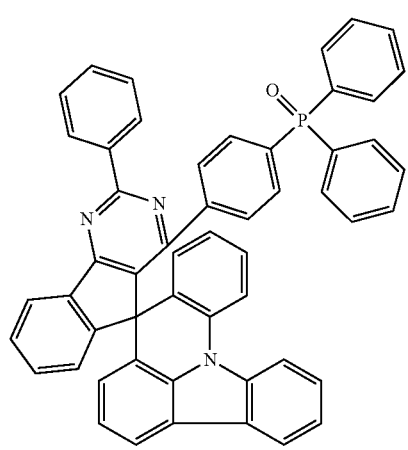
Chemical Formula 1-20
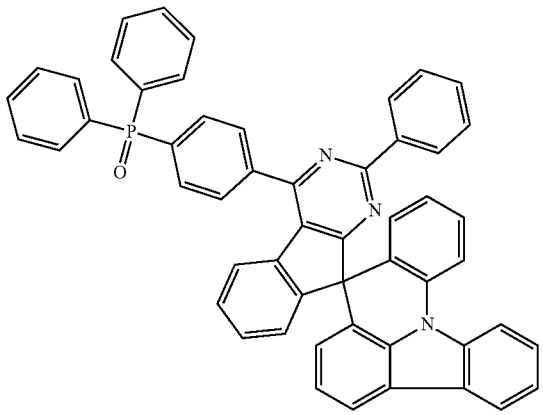
Chemical Formula 1-21
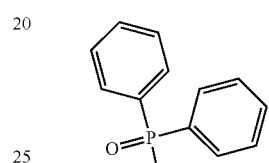
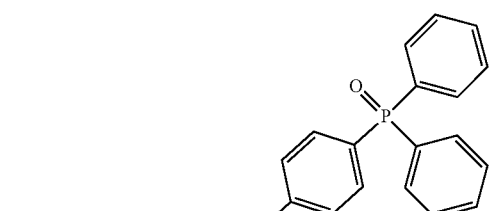
Chemical Formula 1-22
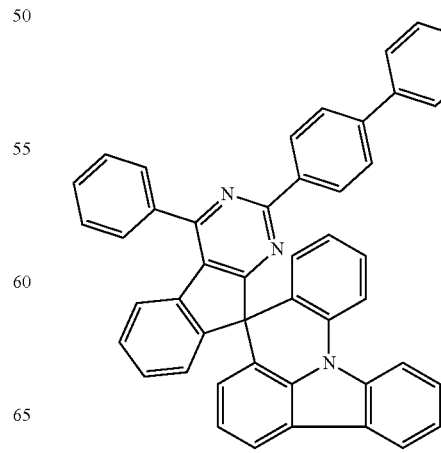

-continued
Chemical Formula 1-23
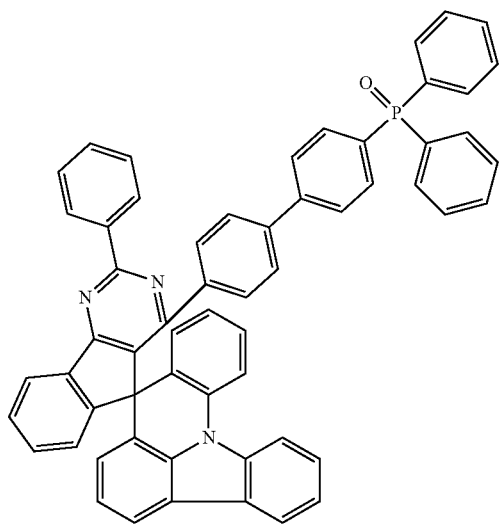
Chemical Formula 1-24
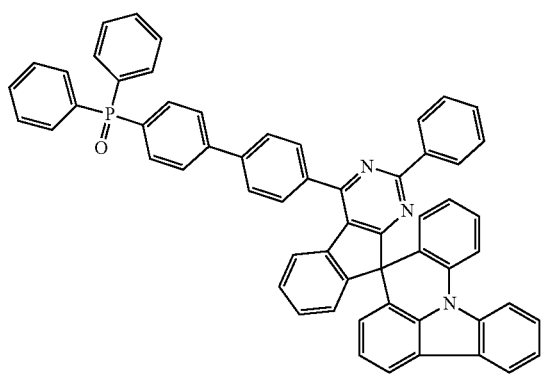
Chemical Formula 1-25
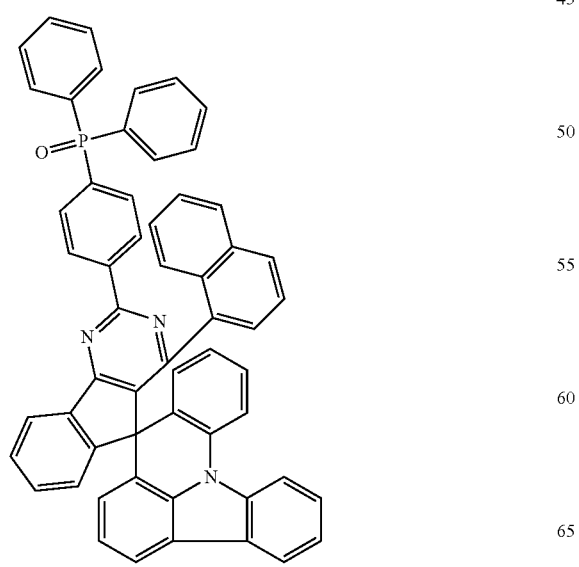
Chemical Formula 1-26
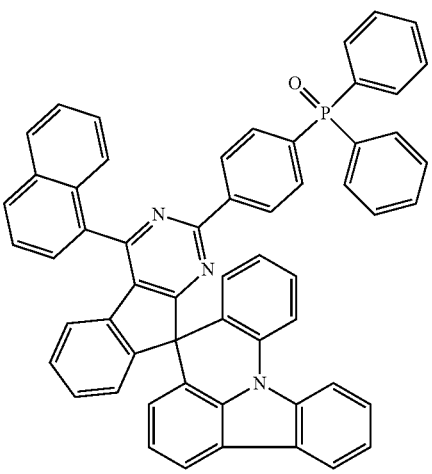
Chemical Formula 1-27
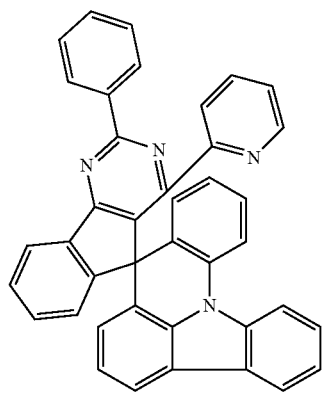
Chemical Formula 1-28
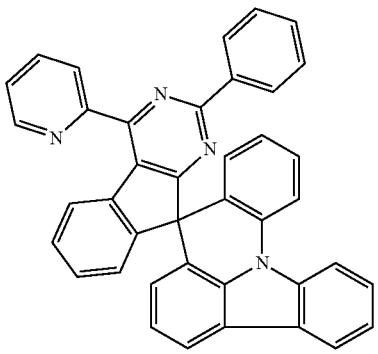

-continued
Chemical Formula 1-29
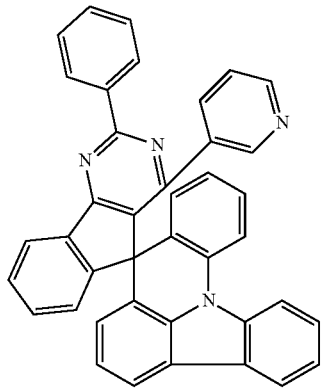
Chemical Formula 1-30
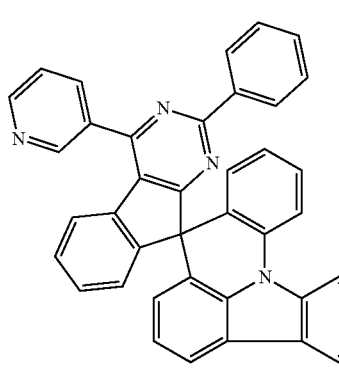
Chemical Formula 1-31
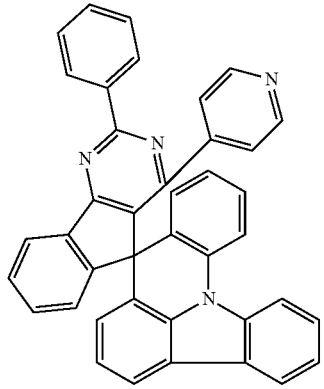
Chemical Formula 1-32
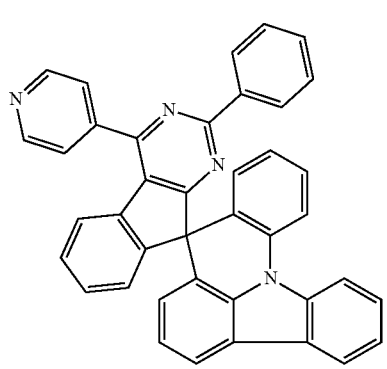
-continued
Chemical Formula 1-33
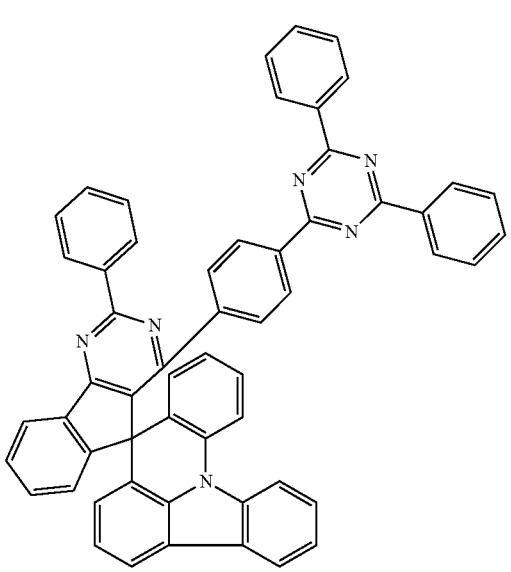
Chemical Formula 1-34
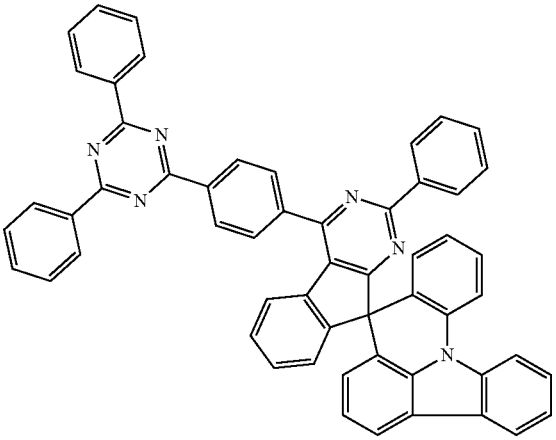
Chemical Formula 1-35
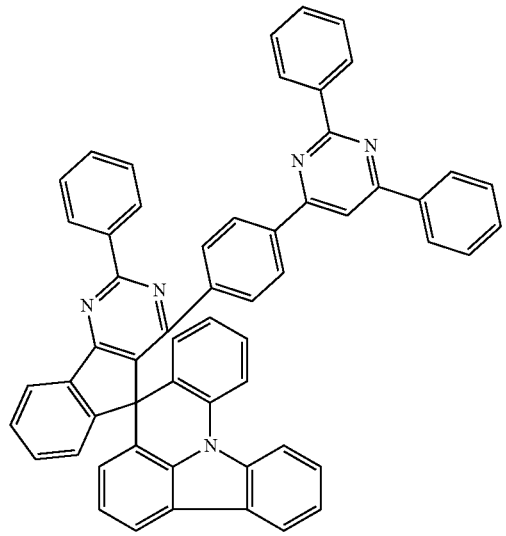

Chemical Formula 1-36
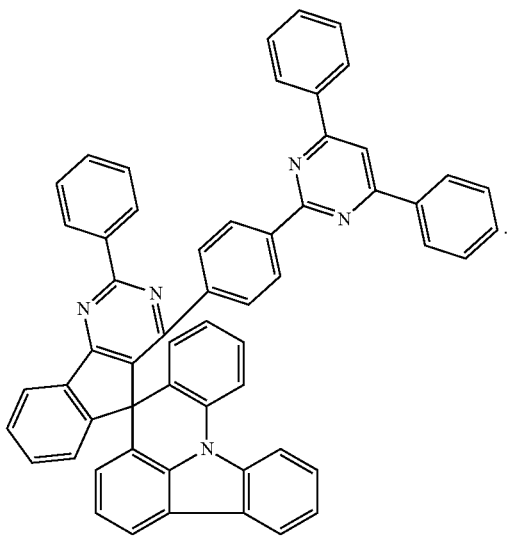
Chemical Formula 2-3
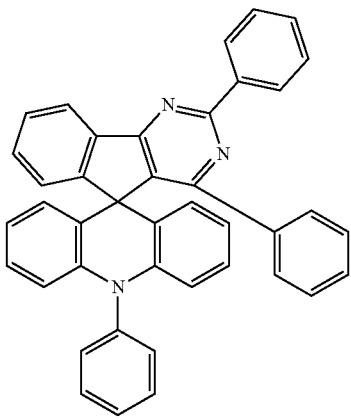
Chemical Formula 2-4
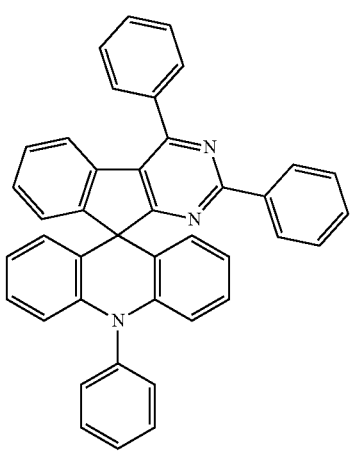
5. The heterocyclic compound of claim 1, wherein the heterocyclic compound represented by Chemical Formula 2 is represented by any one of the following Chemical Formulas 2-1 to 2-32:
Chemical Formula 2-1
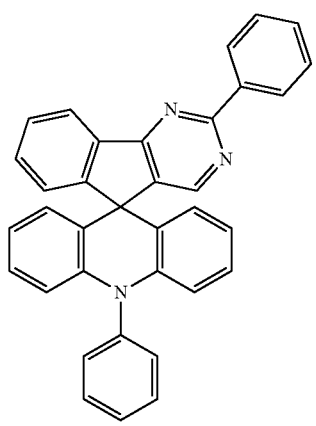
Chemical Formula 2-5
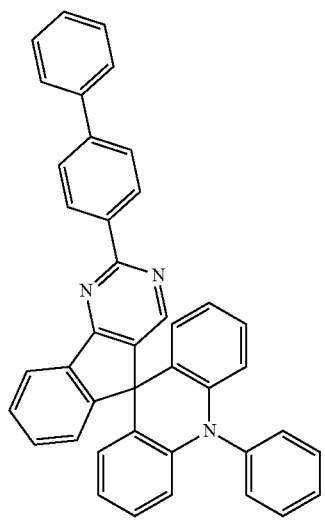
Chemical Formula 2-2
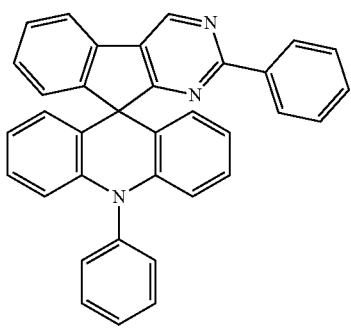

Chemical Formula 2-6
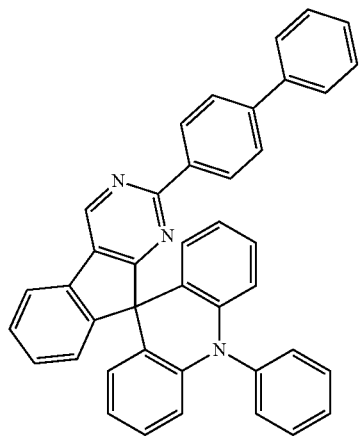
Chemical Formula 2-7
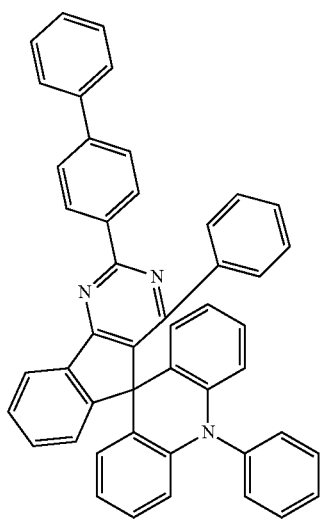
Chemical Formula 2-8
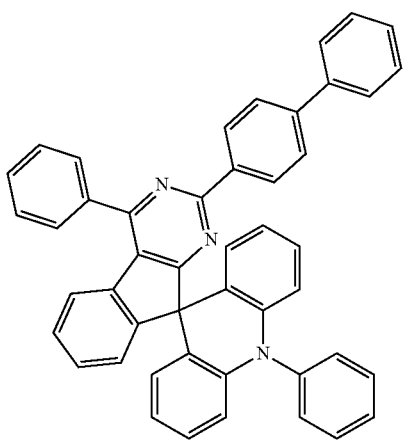
Chemical Formula 2-9
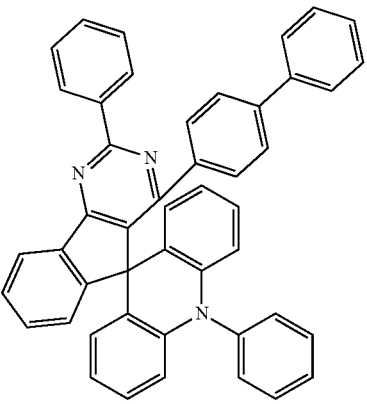
Chemical Formula 2-10
Chemical Formula 2-11
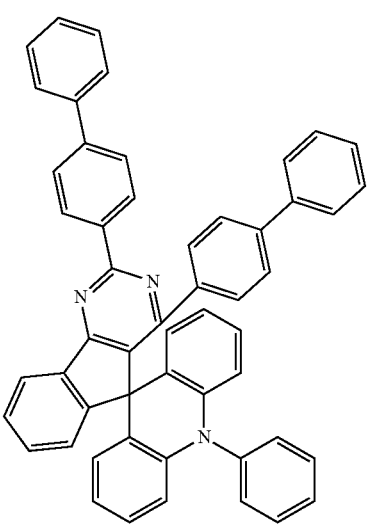

Chemical Formula 2-12
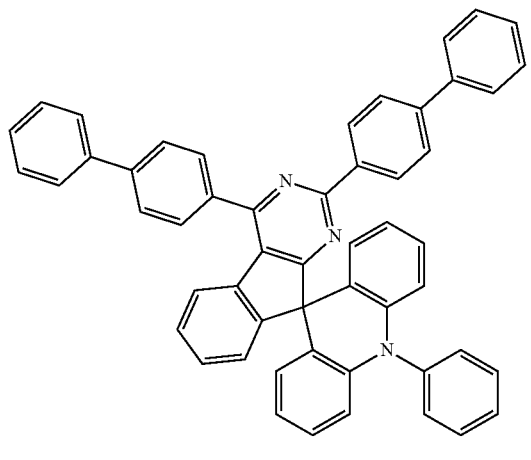
Chemical Formula 2-13
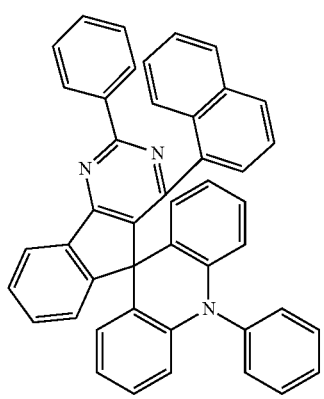
Chemical Formula 2-14
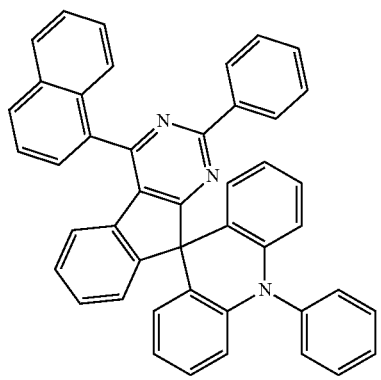
Chemical Formula 2-15
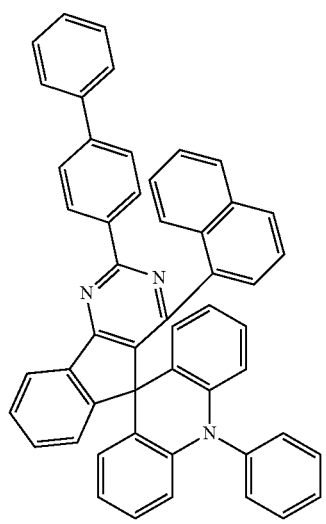
Chemical Formula 2-16
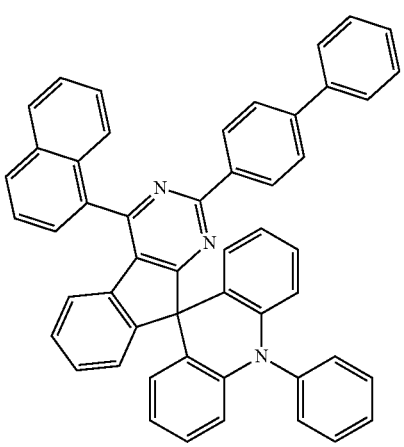
Chemical Formula 2-17
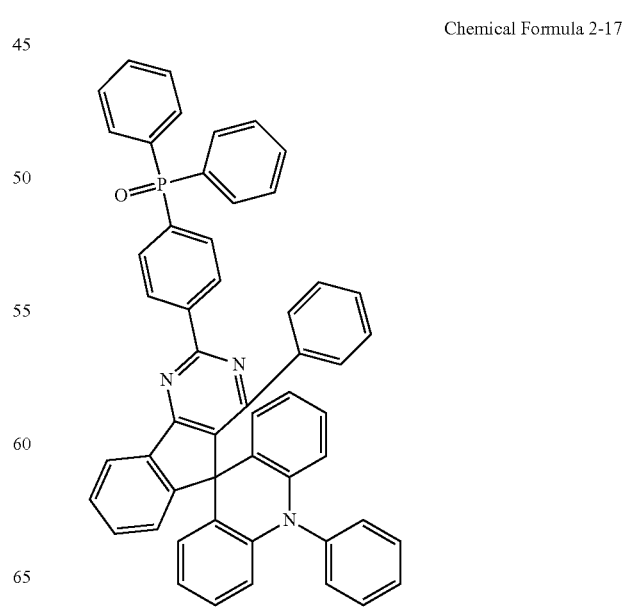

Chemical Formula 2-18
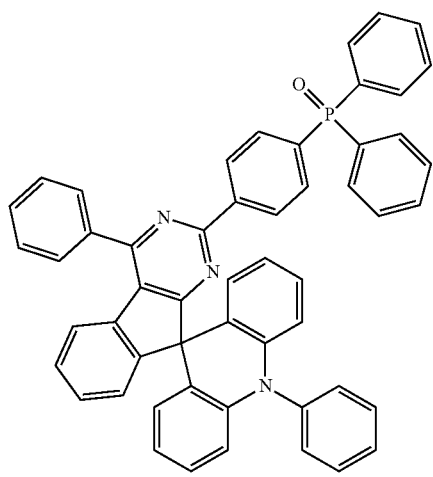
Chemical Formula 2-19
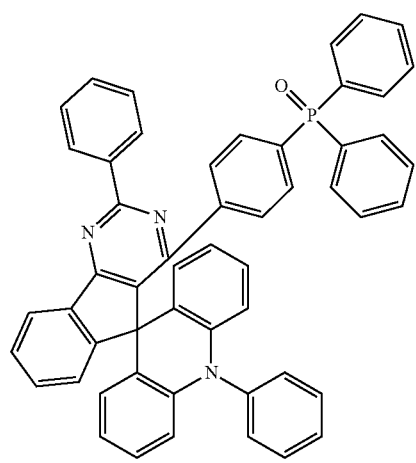
Chemical Formula 2-20
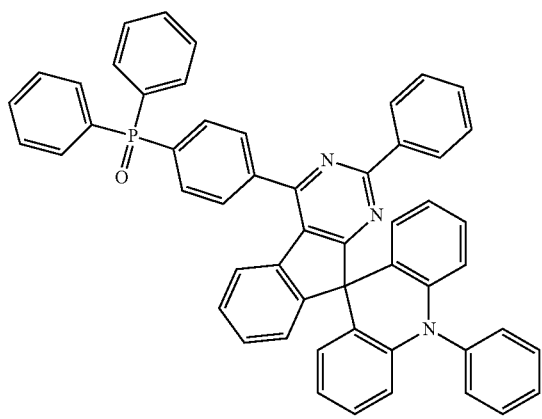
Chemical Formula 2-21
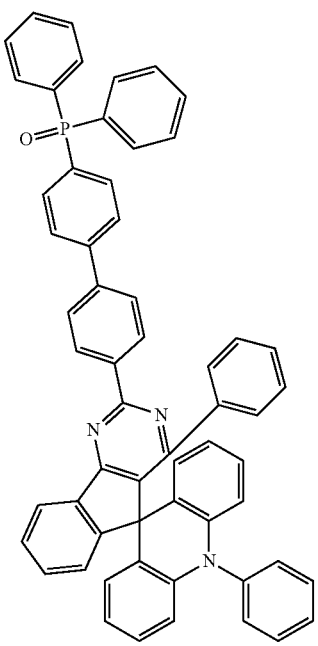
Chemical Formula 2-22
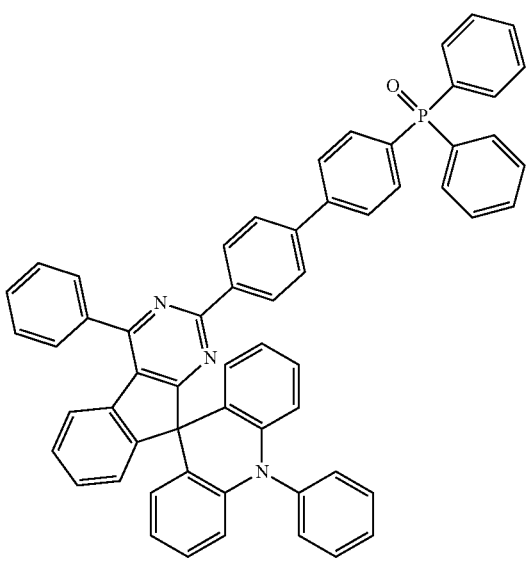

Chemical Formula 2-23
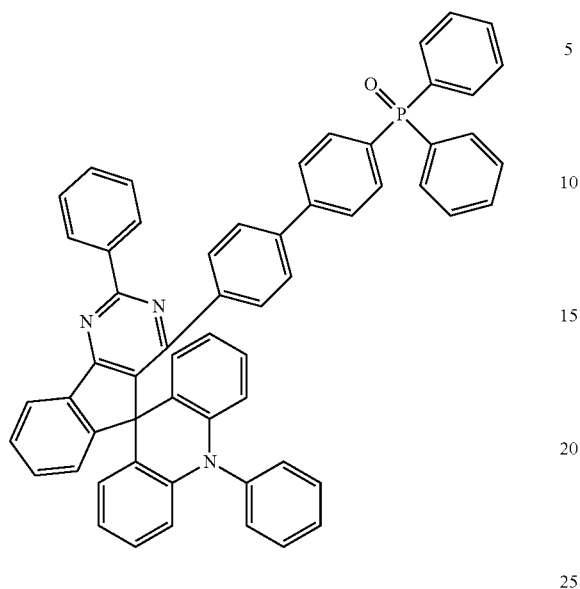
Chemical Formula 2-24
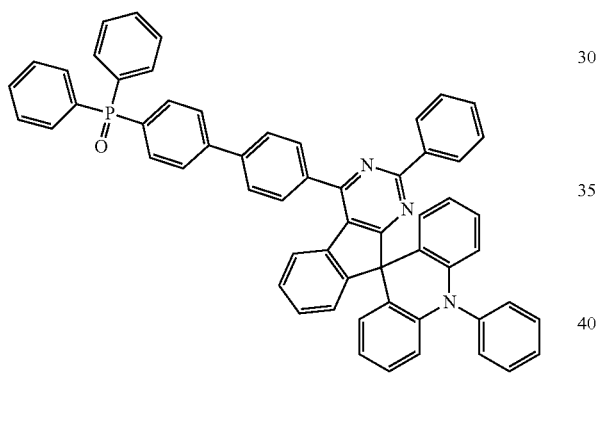
Chemical Formula 2-25
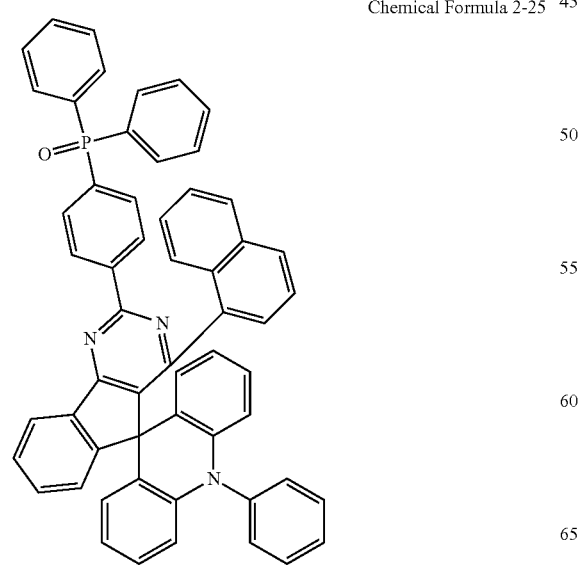
Chemical Formula 2-26
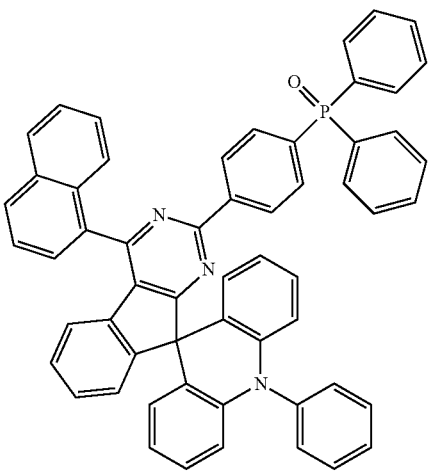
Chemical Formula 2-27
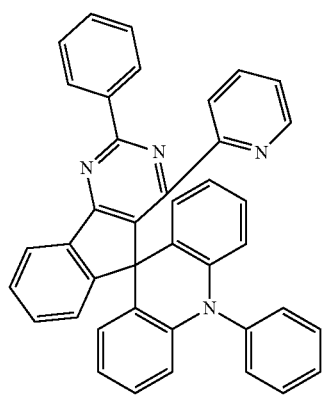
Chemical Formula 2-28
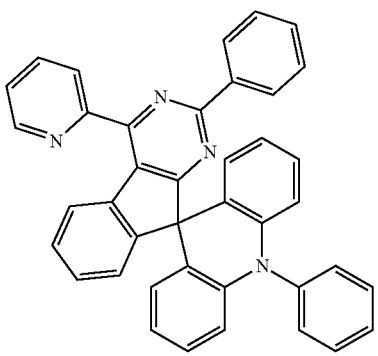

Chemical Formula 2-29

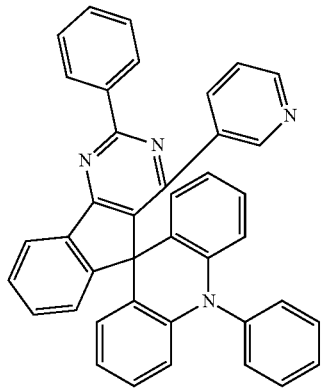

Chemical Formula 2-30

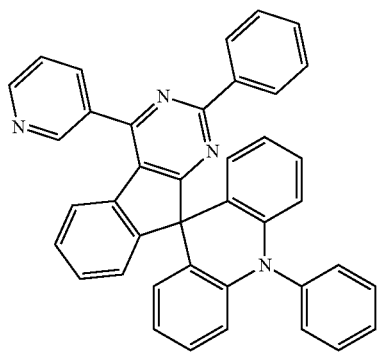

Chemical Formula 2-31

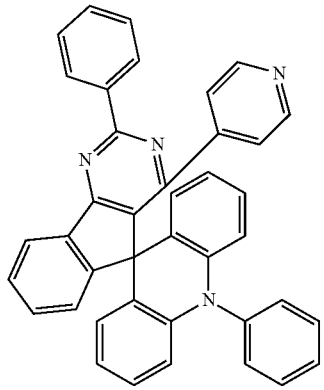

Chemical Formula 2-32

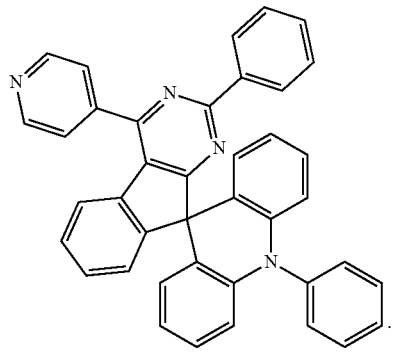

6. An organic light emitting device comprising:
   a first electrode;
   a second electrode; and
   organic material layers formed of one or more layers including a light emitting layer disposed between the first electrode and the second electrode,
   wherein one or more layers of the organic material layers include the heterocyclic compound according to claim 1.

7. The organic light emitting device of claim 6, wherein the organic material layer includes a hole transport layer, a hole injection layer, or a layer where both hole transporting and hole injection are performed, and the hole transport layer, the hole injection layer, or the layer where both the hole transporting and the hole injection are performed includes the heterocyclic compound.

8. The organic light emitting device of claim 6, wherein the organic material layer includes an electron injection layer, and the electron injection layer includes the heterocyclic compound.

9. The organic light emitting device of claim 6, wherein the organic material layer includes an electron transport layer, and the electron transport layer includes the heterocyclic compound.

10. The organic light emitting device of claim 6, wherein the light emitting layer includes the heterocyclic compound.

11. The organic light emitting device of claim 6, wherein the organic material layer includes the heterocyclic compound as a host, and another organic compound, a metal, or a metal compound as a dopant.

12. The organic light emitting device of claim 6, wherein the organic material layer further includes one layer or two or more layers selected from the group consisting of a hole injection layer, a hole transport layer, an electron transport layer, an electron injection layer, an electron blocking layer, and a hole blocking layer.

* * * * *